US010856852B2

(12) United States Patent
Azuma et al.

(10) Patent No.: US 10,856,852 B2
(45) Date of Patent: Dec. 8, 2020

(54) ULTRASONIC DIAGNOSTIC SYSTEM AND ULTRASONIC DIAGNOSTIC METHOD

(71) Applicants: The University of Tokyo, Tokyo (JP); Lily Medtech, Inc., Tokyo (JP)

(72) Inventors: Takashi Azuma, Tokyo (JP); Hirofumi Nakamura, Tokyo (JP)

(73) Assignees: The University of Tokyo, Tokyo (JP); Lily Medtech, Inc., Tokyo (JP)

( * ) Notice: Subject to any disclaimer, the term of this patent is extended or adjusted under 35 U.S.C. 154(b) by 487 days.

(21) Appl. No.: 15/934,796

(22) Filed: Mar. 23, 2018

(65) Prior Publication Data

US 2018/0206827 A1    Jul. 26, 2018

Related U.S. Application Data

(63) Continuation-in-part of application No. PCT/JP2016/078115, filed on Sep. 23, 2016.

(30) Foreign Application Priority Data

Sep. 24, 2015    (JP) .................................. 2015-187024

(51) Int. Cl.
  *A61B 8/00*      (2006.01)
  *A61B 8/06*      (2006.01)
  (Continued)

(52) U.S. Cl.
  CPC .................. *A61B 8/54* (2013.01); *A61B 8/06* (2013.01); *A61B 8/08* (2013.01); *A61B 8/0825* (2013.01);
  (Continued)

(58) Field of Classification Search
  CPC ........... A61B 8/54; A61B 8/08; A61B 8/0825; A61B 8/15; A61B 8/406; A61B 8/0891;
  (Continued)

(56) References Cited

U.S. PATENT DOCUMENTS 4,074,564 A * 2/1978 Anderson ............ A61B 8/0875
                                                    73/596
2003/0100832 A1    5/2003 Criton et al.
(Continued)

FOREIGN PATENT DOCUMENTS

CN    102204831 A    10/2011
CN    103190931 A    7/2013
(Continued)

OTHER PUBLICATIONS

International Search Report for PCT/JP2016/078115 dated Nov. 22, 2016.
(Continued)

*Primary Examiner* — Peter Luong

(57) ABSTRACT

An ultrasonic diagnostic system includes elements disposed around a subject to transmit and/or receive ultrasonic waves. A controller controls the elements so that some of the elements disposed in a first region transmit ultrasonic waves at a first angle to a diagnosis target in the subject, some of the elements disposed in a second region receive reflected waves of the ultrasonic waves, which are reflected from the diagnosis target at a second angle, and some of the elements disposed in a third region receive reflected waves of the ultrasonic waves, which are reflected from the diagnosis target at a third angle distinct from the second angle. An operator calculates a velocity vector of the diagnosis target using the reflected waves received by the some of the elements disposed in the second region and the reflected waves received by the some of the elements disposed in the third region.

18 Claims, 17 Drawing Sheets

(51) Int. Cl.
*A61B 8/14* (2006.01)
*A61B 8/08* (2006.01)
*A61B 8/15* (2006.01)

(52) U.S. Cl.
CPC .............. *A61B 8/0891* (2013.01); *A61B 8/14* (2013.01); *A61B 8/15* (2013.01); *A61B 8/406* (2013.01); *A61B 8/56* (2013.01); *A61B 8/463* (2013.01); *A61B 8/488* (2013.01)

(58) Field of Classification Search
CPC .... A61B 8/56; A61B 8/06; A61B 8/14; A61B 8/463; A61B 8/488
See application file for complete search history.

(56) References Cited

U.S. PATENT DOCUMENTS

| | | | | |
|---|---|---|---|---|
| 2005/0277835 | A1* | 12/2005 | Angelsen | A61B 8/485 600/437 |
| 2009/0178483 | A1* | 7/2009 | Angelsen | G01S 7/52095 73/597 |
| 2011/0245673 | A1 | 10/2011 | Kamiyama | |
| 2013/0178743 | A1 | 7/2013 | Shim et al. | |
| 2017/0181638 | A1* | 6/2017 | Nanaumi | A61B 8/0825 |

FOREIGN PATENT DOCUMENTS

| | | |
|---|---|---|
| JP | 05203335 A | 2/1993 |
| JP | H0549639 A | 3/1993 |
| JP | 2003164453 A | 6/2003 |
| JP | 2005185763 A | 7/2005 |
| JP | 2006055493 A | 3/2006 |
| JP | 2013165922 A | 8/2013 |
| WO | WO2014191784 A1 | 12/2014 |

OTHER PUBLICATIONS

Jorgen Arendt Jensen et al., "A New Method for Estimation of Velocity Vectors", IEEE Transactions on Ultrasonics, Ferroelectrics and Frequency Control, May 1998, pp. 837-851, vol. 45.

* cited by examiner

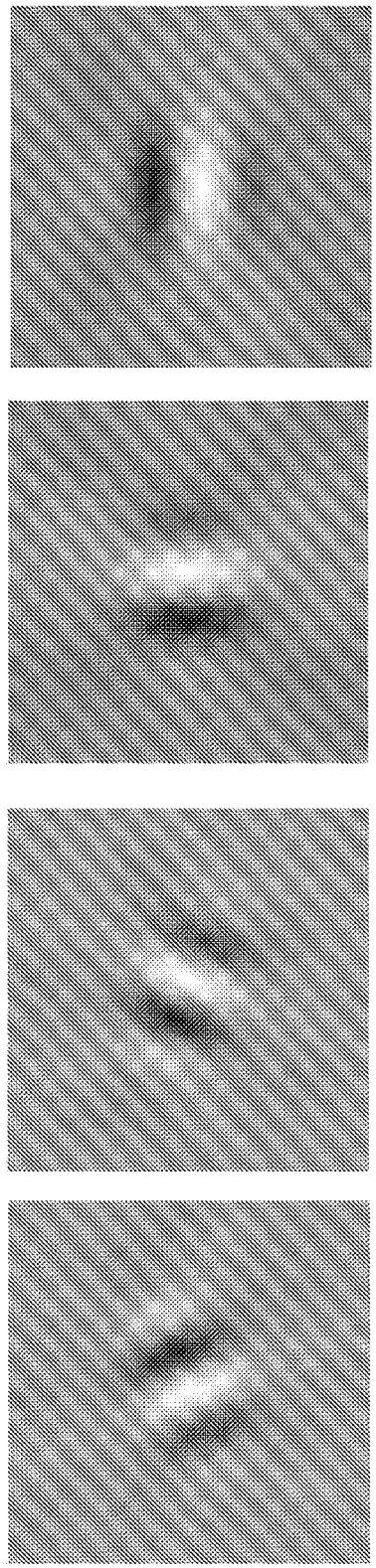

ULTRASONIC DIAGNOSTIC SYSTEM AND ULTRASONIC DIAGNOSTIC METHOD

CROSS-REFERENCE TO RELATED APPLICATIONS

The present application is a by-pass continuation application of International Application No. PCT/JP2016/078115 filed on Sep. 23, 2016, which claims priority to Japanese Patent Application No. 2015-187024 filed on Sep. 24, 2015, the contents of which are incorporated herein by reference in their entirety.

BACKGROUND OF THE INVENTION

Field of the Invention

The present invention relates to an ultrasonic diagnostic system and an ultrasonic diagnostic method.

Discussion of the Background

Ultrasonic diagnostic systems are noninvasive, that is, do not require a surgical operation in which a living body undergo incision to observe directly. Because of the noninvasive nature, ultrasonic diagnostic systems are widely used in the medical field as a technique to diagnose internal information of a subject.

In a conventional ultrasonic diagnostic system, a tomography image of a subject is created by radiating ultrasonic waves to the subject and analyzing reflected waves from the subject. Since sound is a compressional wave, sound pressure of an ultrasonic wave propagates by fluctuation in a traveling direction of the ultrasonic wave. In an ultrasonic diagnosis, echo signals scattered by scatterers in In an ultrasonic diagnosis, echo signals scattered by scatterers in a subject are received. By measuring a fluctuation of an echo signal caused by movement of a scatterer, the conventional ultrasonic diagnostic system can detect a movement of an object.

For example, a diagnostic device described in Patent Document 1 includes an ultrasonic probe configured to transmit ultrasonic waves at a right angle to a beating blood vessel, and to receive a reflective echo, and performs signal processing to extract, from the reflected echo, a component that is frequency-shifted due to the Doppler effect. The diagnostic device described in Patent Document 1 calculates a blood flow velocity by using the reflective echo as a detection signal.

The contents of Japanese Unexamined Patent Application Publication No. 05-023335 are incorporated herein by reference in their entirety.

The contents of IEEE Trans. Ultrason. Ferr. Freq. Contrl., vol. 45 No. 3 pp. 837-851, 1998 are incorporated herein by reference in their entirety.

A change in an echo signal is not however significant when an object moves in a direction perpendicular to a direction in which ultrasonic waves advance, compared with that when the object moves along the direction in which the ultrasonic waves advance. Such an ordinary ultrasonic device as described in Patent Document 1 can therefore detect a movement of a subject only by components in relation to a direction along which ultrasonic waves are transmitted.

With regard to methods for measuring a Doppler blood flow as a vector, Non-patent Document 1, for example, proposes a method for applying a phase modulation in a direction of an aperture for transmission and reception and a method for setting two beams at angles different from each other in a linear or sector probe. A problem in the former method is a reduction in transmission energy. A problem in the latter method is a reduction in an angle formed by the two beams that are set at angles different from each other in the probe when they reach a deeper section in the subject. This results in that no vector can be measured when a diagnosis target presents at a deeper section.

SUMMARY OF THE INVENTION

According to one aspect of the present invention, an ultrasonic diagnostic system includes a plurality of elements, a controller, and an operator. The plurality of elements is disposed around a subject. The plurality of elements is configured to transmit and/or receive ultrasonic waves. The controller is configured to control the plurality of elements so that at least some of elements disposed in a first region, among the plurality of elements, transmit ultrasonic waves at a first angle to a diagnosis target in the subject, at least some of elements disposed in a second region, among the plurality of elements, receive reflected waves of the ultrasonic waves, the reflected waves being reflected from the diagnosis target at a second angle, and at least some of elements disposed in a third region, among the plurality of elements, receive reflected waves of the ultrasonic waves, the reflected waves being reflected from the diagnosis target at a third angle distinct from the second angle. The operator is configured to calculate a velocity vector of the diagnosis target using the reflected waves received by the at least some of the elements disposed in the second region and the reflected waves received by the at least some of the elements disposed in the third region.

According to another aspect of the present invention, an ultrasonic diagnostic system includes a plurality of elements, a controller, and an operator. The plurality of elements is disposed around a subject. The plurality of elements is configured to transmit and/or receive ultrasonic waves. The controller is configured to control the plurality of elements so that at least some of elements disposed in a first region, among the plurality of elements, transmit first ultrasonic waves at a first angle toward a diagnosis target in the subject, the at least some of the elements disposed in the first region, among the plurality of elements, receive reflected waves of the first ultrasonic waves, the reflected waves being reflected from the diagnosis target at the first angle, at least some of elements disposed in a second region, among the plurality of elements, transmit second ultrasonic waves at a second angle toward the diagnosis target, and the at least some of the elements disposed in the second region, among the plurality of elements, receive reflected waves of the second ultrasonic waves, the reflected waves being reflected from the diagnosis target at the second angle. The operator is configured to calculate a velocity vector of the diagnosis target using the reflected waves received by the at least some of the elements disposed in the first region and the reflected waves received by the at least some of the elements disposed in the second region.

According to another aspect of the present invention, an ultrasonic diagnostic system includes a plurality of elements, a controller, and an operator. The plurality of elements is disposed around a subject. The plurality of elements is configured to transmit and/or receive ultrasonic waves. The controller is configured to control the plurality of elements so that at least some of elements disposed in a first region, among the plurality of elements, receive reflected waves of first ultrasonic waves, the reflected waves being reflected from a diagnosis target in the subject, and at least some of elements disposed in a second region, among the plurality of elements, receive reflected waves of second ultrasonic waves, the reflected waves being reflected from the diagnosis target. The operator is configured to capture a first image using the reflected waves of the first ultrasonic waves, the reflected waves being received by the at least some of the elements disposed in the first region, to capture a second image using the reflected waves of the second ultrasonic waves, the reflected waves being received by the at least some of the elements disposed in the second region, to calculate two matrices for the respective first and second images in each of which vectors formed by rearranging the image are rearranged in a time direction, to calculate a third matrix in which the two matrices are arranged in a direction perpendicular to the time direction, and to extract information on blood flows in the diagnosis target from the third matrix.

According to another aspect of the present invention, an ultrasonic diagnostic system includes a plurality of elements, a controller, and an operator. The plurality of elements is disposed around a subject. The plurality of elements is configured to transmit and/or receive ultrasonic waves. The controller is configured to control the plurality of elements so that at least elements disposed in a first region, among the plurality of elements, transmit first ultrasonic waves toward a diagnosis target in the subject, and at least elements disposed in a second region, among the plurality of elements, transmit second ultrasonic waves toward the diagnosis target. The operator is configured to capture a first image using reflected waves of the first ultrasonic waves transmitted from the elements disposed in the first region, to capture a second image using reflected waves of the second ultrasonic waves transmitted from the elements disposed in the second region, to calculate two matrices for the respective first and second images in each of which vectors formed by rearranging the image are rearranged in a time direction, to calculate a third matrix in which the two matrices are arranged in a direction perpendicular to the time direction, and to extract information on blood flows in the diagnosis target from the third matrix.

According to another aspect of the present invention, an ultrasonic diagnostic method is performed by using a diagnostic device that includes a plurality of elements disposed around a subject. The plurality of elements is configured to transmit and/or receive ultrasonic waves. The ultrasonic diagnostic method includes controlling the plurality of elements so that at least some of elements disposed in a first region, among the plurality of elements, transmit ultrasonic waves at a first angle to a diagnosis target in the subject, at least some of elements disposed in a second region, among the plurality of elements, receive reflected waves of the ultrasonic waves, the reflected waves being reflected from the diagnosis target at a second angle, and at least some of elements disposed in a third region, among the plurality of elements, receive reflected waves of the ultrasonic waves, the reflected waves being reflected from the diagnosis target at a third angle distinct from the second angle. A velocity vector of the diagnosis target is calculated using the reflected waves received by the at least some of the elements disposed in the second region and the reflected waves received by the at least some of the elements disposed in the third region.

According to another aspect of the present invention, an ultrasonic diagnostic method is performed by using a diagnostic device that includes a plurality of elements disposed around a subject. The plurality of elements is configured to transmit and/or receive ultrasonic waves. The ultrasonic diagnostic method includes controlling the plurality of elements so that at least some of elements disposed in a first region, among the plurality of elements, transmit first ultrasonic waves at a first angle toward a diagnosis target in the subject, the at least some of the elements disposed in the first region, among the plurality of elements, receive reflected waves of the first ultrasonic waves, the reflected waves being reflected from the diagnosis target at the first angle, at least some of elements disposed in a second region, among the plurality of elements, transmit second ultrasonic waves at a second angle toward the diagnosis target, and the at least some of the elements disposed in the second region, among the plurality of elements, receive reflected waves of the second ultrasonic waves, the reflected waves being reflected from the diagnosis target at the second angle. A velocity vector of the diagnosis target is calculated using the reflected waves received by the at least some of the elements disposed in the first region and the reflected waves received by the at least some of the elements disposed in the second region.

According to another aspect of the present invention, an ultrasonic diagnostic system includes a plurality of elements, a controller, and an operator. The plurality of elements is disposed around a subject. The plurality of elements is configured to transmit and/or receive ultrasonic waves. The controller is configured to control the plurality of elements so that elements configuring a part of the plurality of elements transmit ultrasonic waves toward a diagnosis target in the subject, and reflected waves of the ultrasonic waves from the diagnosis target are received by two or more apertures disposed in regions where angles of reflection from the diagnosis target differ from each other. The operator is configured to calculate a velocity vector of the diagnosis target using the reflected waves respectively received by groups of elements configuring the two or more apertures.

According to the other aspect of the present invention, an ultrasonic diagnostic system includes a plurality of elements, a controller, and an operator. The plurality of elements is disposed around a subject. The plurality of elements is configured to transmit and/or receive ultrasonic waves. The controller is configured to control the plurality of elements so that elements disposed in a first region, among the plurality of elements, transmit first ultrasonic waves toward a diagnosis target in the subject, the elements disposed in the first region receive reflected waves of the first ultrasonic waves, the reflected waves being reflected from the diagnosis target, elements disposed in a second region, among the plurality of elements, transmit second ultrasonic waves toward the diagnosis target, and the elements disposed in the second region receive reflected waves of the second ultrasonic waves, the reflected waves being reflected from the diagnosis target. The operator is configured to calculate a velocity vector of the diagnosis target using the reflected waves of the first and second ultrasonic waves.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIGS. 9A to 9D show photos indicative of spatial distributions in sensitivity of transmission and reception adjacent to focus points, according to the embodiment of the present invention;

DESCRIPTION OF THE EMBODIMENTS

An embodiment of the present invention will now be described herein in detail. The below embodiment is merely an example intended to describe the present invention. The present invention is thus not limited only to the embodiment. The present invention can also be variously modified within the scope and spirit of the present invention. Those skilled in the art can apply an embodiment with components that are equivalent to and replaced from the components described below. Such an embodiment is also included in the scope and spirit of the present invention. Sizes and ratios are also not limited to the sizes and ratios applied in the accompanied drawings.

Embodiment

An ultrasonic diagnostic system 10 according to an embodiment of the present invention is configured, as a system, to radiate ultrasonic waves toward a subject, such as human body, to use reflected waves reflected from the subject (a signal acquired by analyzing a plurality of reflected waves acquired at different times from a single location to extract a time-change component of a target will be hereinafter also referred to as "Doppler signal"), and to capture an image of a piece of tissue in the subject, in particular a blood flow. A subject may be a human body or its component, such as a hand, an arm, a leg, a buttock, and breasts. The ultrasonic diagnostic system 10 according to the embodiment can measure a flow amount and a flow velocity of blood flowing in a subject T. In a location in which a cancer cell is generated, a blood vessel is newly formed, which is called a new blood vessel, increasing blood vessel density. The ultrasonic diagnostic system 10 can measure a blood flow amount and a blood flow velocity to image a result of measurement. A medical doctor can diagnose a lesion, such as a malignant tumor (A malignant tumor will be hereinafter also referred to as "cancer".), by checking an image captured by the ultrasonic diagnostic system 10. A configuration of the ultrasonic diagnostic system 10 will now be described herein with reference to FIG. 1.

Figure 1:
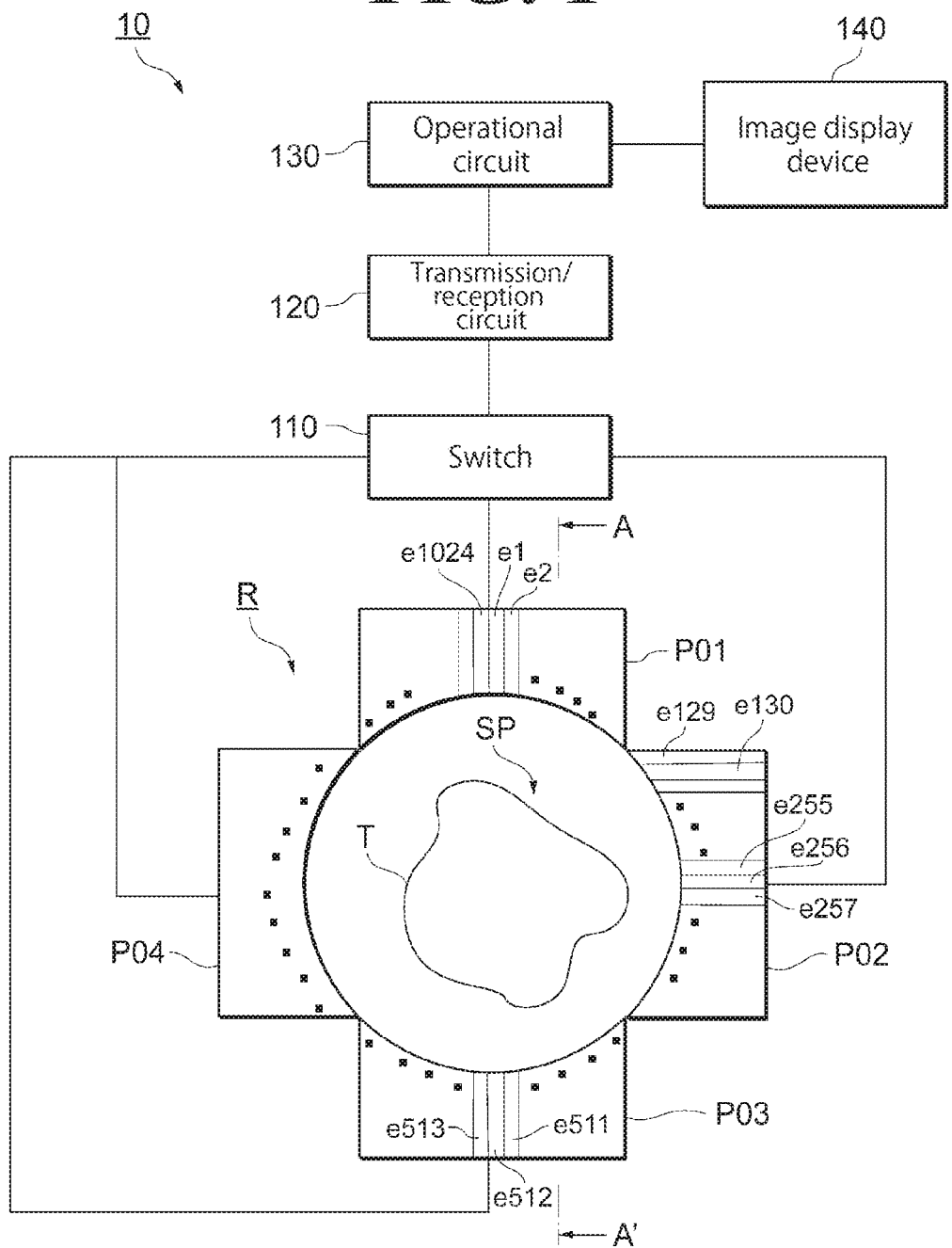
FIG. 1 is a block diagram of an ultrasonic diagnostic system according to an embodiment of the present invention, the block diagram schematically illustrating a configuration.

As illustrated in FIG. 1, the ultrasonic diagnostic system 10 includes a ring array R, a switch 110, a transmission/reception circuit 120, an operational circuit (an example operator) 130, and an image display device 140.

The ring array R is a ring-shaped oscillator in which a plurality of oscillators are combined. The ring array R may have a diameter falling in a range from 80 to 500 mm inclusive, advantageously, or a diameter falling in a range from 100 to 300 mm inclusive, more advantageously. The ring array R may otherwise have a variable diameter. The embodiment uses, as an example, a ring-shaped oscillator having a diameter of 200 mm, in which four concave transducers P01 to P04 are combined. In this example, the recessed surface type oscillators P01 to P04 each includes 256 rectangular piezo-electric elements (hereinafter also simply referred to as "elements".). The number of elements configuring each of the oscillators is not limited, but may range from 1 to 1000, advantageously, or from 100 to 500, more advantageously. In the embodiment, the elements each have a function for converting an electric signal into an ultrasonic wave signal, or vice versa. The elements each transmit ultrasonic waves to the subject T, receive reflected waves (Doppler signals) reflected from the subject T, and form electric signals as reception data. In the embodiment, the elements are described to each function as both a transmission element that transmits ultrasonic waves and a reception element that receives ultrasonic waves. However, the elements are not limited to each have the functions. For example, each element may be either a transmission element or a reception element, and a plurality of transmission elements and a plurality of reception elements may respectively be disposed in a ring shape. For another example, the configuration may be a combination of elements each functioning as both a transmission element and a reception, elements with transmission function only, and elements with reception function only.

Although FIG. 1 only illustrates a partial view, the recessed surface type oscillator P01 includes 256 elements, i.e., elements e1 to e128 and elements e897 to e1024, the recessed surface type oscillator P02 includes 256 elements, i.e., elements e129 to e384, the recessed surface type oscillator P03 includes 256 elements, i.e., elements e385 to e640, and the recessed surface type oscillator P04 includes 256 elements, i.e., elements e641 to e896. The elements e1 to e1024 are disposed in a clockwise direction along the ring in an ascending order of number around an insertion portion SP evenly at an interval of approximately 0.352 degrees. Hereinafter, positions of the elements are described as follows: a position at which the element e1 is disposed is defined to 0 degrees, a clockwise range from the elements e1 to e512 is defined to an angle range from 0 degrees to 180 degrees, and a counterclockwise range from the elements e1 to e512 is defined to an angle range from 0 degrees to −180 degrees.

At a center of the ring array R, the insertion portion SP into which the subject T is to be inserted is provided. A diameter is not limited, but may range from 70 to 490 mm, advantageously, or may range from 90 to 290 mm, more advantageously. In the embodiment, as an example, a diameter of approximately 100 mm is specified. On an inner circumference side of the ring array R, a convex lens called an acoustic lens is attached. Such a surface-finishing on the inner circumference side of the ring array allows R to converge ultrasonic waves transmitted from the elements to a plane including the ring array R. The number of elements configuring the ring array R and a diameter are not limited to the number and the diameter illustrated in FIG. 1. In the example, the elements are disposed in a ring shape at even intervals. However, the shape of the ring array R is not limited to a circular shape, but may be a desired polygonal shape, such as hexagonal shape, square shape, and triangular shape, a shape at least partially including a curve or an arc, or another desired shape, or a part of one of the aforementioned shapes (e.g., semicircle or arc), for example. In other words, the ring array R may be generalized to "array R". The elements configuring the array R may be advantageously disposed so as to intermittently surround the subject T in an angle range of at least 90 degrees or greater. However, this is merely an example. In the present invention, as long as the elements each transmit and receive ultrasonic waves at various angles toward and from a subject, the plurality of elements may be at least disposed around the subject, and may not be disposed to form a single array.

The ring array R is coupled to the transmission/reception circuit 120 via the switch 110.

The transmission/reception circuit 120 is configured to transmit control signals (which are electric signals) to the elements of the ring array R to control how ultrasonic waves are transmitted and received. For example, the transmission/reception circuit 120 sends, to the elements, instructions on a frequency, a magnitude, and a wave type (e.g., continuous wave and pulse wave) of ultrasonic waves to be transmitted, as well as the number of pieces of reception data to be collected from the elements, which will be used by the operational circuit 130 to measure a blood flow amount and a blood flow velocity (the number of pieces of reception data to be collected, i.e., the number of transmissions/receptions in a plurality of transmissions/receptions to be performed to acquire a time-change component in data from a single portion in a subject T for use in computation will be hereinafter also referred to as "packet count", described later. In the embodiment, as an example, a packet count is specified to eight, and the transmission/reception circuit 120 transmits a control signal driving 256 elements at a time.

The switch 110 is coupled to each of the 1024 elements of the ring array R, and is configured to convey a signal sent from the transmission/reception circuit 120 to desired elements to drive the elements. (An element that has received a control signal will be hereinafter also referred to as a "driven element".) The switch 110 delivers a control signal given by the transmission/reception circuit 120 to 256 elements to be driven, among the 1024 elements. The ultrasonic diagnostic system 10 according to the embodiment uses the switch 110 to sequentially switch driven elements to be coupled to the transmission/reception circuit 120 to achieve driving of the 1024 elements configuring the ring array R. It is advantageous that the switch 110 perform switching at a speed in a smaller order of magnitude than a several millisecond. The ultrasonic diagnostic system 10 can therefore collect data in a near real-time manner.

The operational circuit 130 is configured to analyze Doppler signals received by the elements to measure a flow amount and a flow velocity of blood flow in the subject T. The operational circuit 130 may use the measured flow amount or the measured flow velocity to generate a tomographic image of the subject T. The image display device 140 is a monitor that displays a captured image generated by the operational circuit 130.

Figure 2:
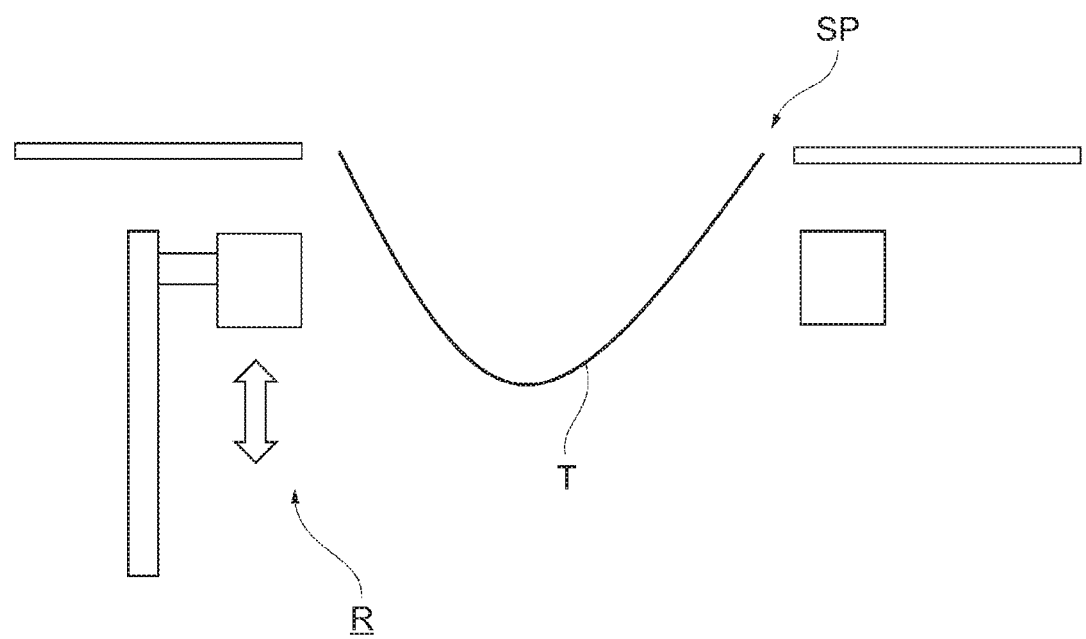
FIG. 2 is a cross-sectional view of the ultrasonic diagnostic system taken along the line A-A' of FIG. 1.

FIG. 2 is a cross-sectional view of the ring array R taken along the line A-A'. As an example, the ring array R is placed under a bed having an opening, so that the opening of the bed and the insertion portion SP are aligned to each other. A research subject inserts a portion of a body, for which an image will be captured, via the opening of the bed, into the insertion portion SP.

Upon the elements receive reception data by an amount corresponding to a packet count specified in the transmission/reception circuit 120, the ring array R moves up or down in the directions shown by arrows in FIG. 2 to change a focus position for transmission/reception and then again receives reception data at an amount corresponding to the packet count. By shifting the focus position and repeating scanning until reception data for an imaging view field is collected as described above (moving the focus position to collect reception data will be hereinafter also referred to as "scan"), two-dimensional round-sliced images can be captured and created.

Next, how the ultrasonic diagnostic system 10 according to the embodiment configured as described above operates will now be described herein.

Blood Flow Amount Measurement Process

A blood flow amount measurement process performed by the ultrasonic diagnostic system 10 will now first be described herein.

In here, measuring a blood flow amount by transmitting and receiving ultrasonic waves using a wave transmission/reception surface formed by all or approximately all of the elements configuring the ring array R (hereinafter referred to as "full aperture") will now be described. The transmission/reception circuit 120 according to the embodiment is configured so that the number of elements that can be controlled simultaneously is 256. When the switch 110 repeats four times driving of each of four groups of the elements one by one, the ultrasonic diagnostic system 10 can therefore collect reception data for the full aperture.

Figure 3:
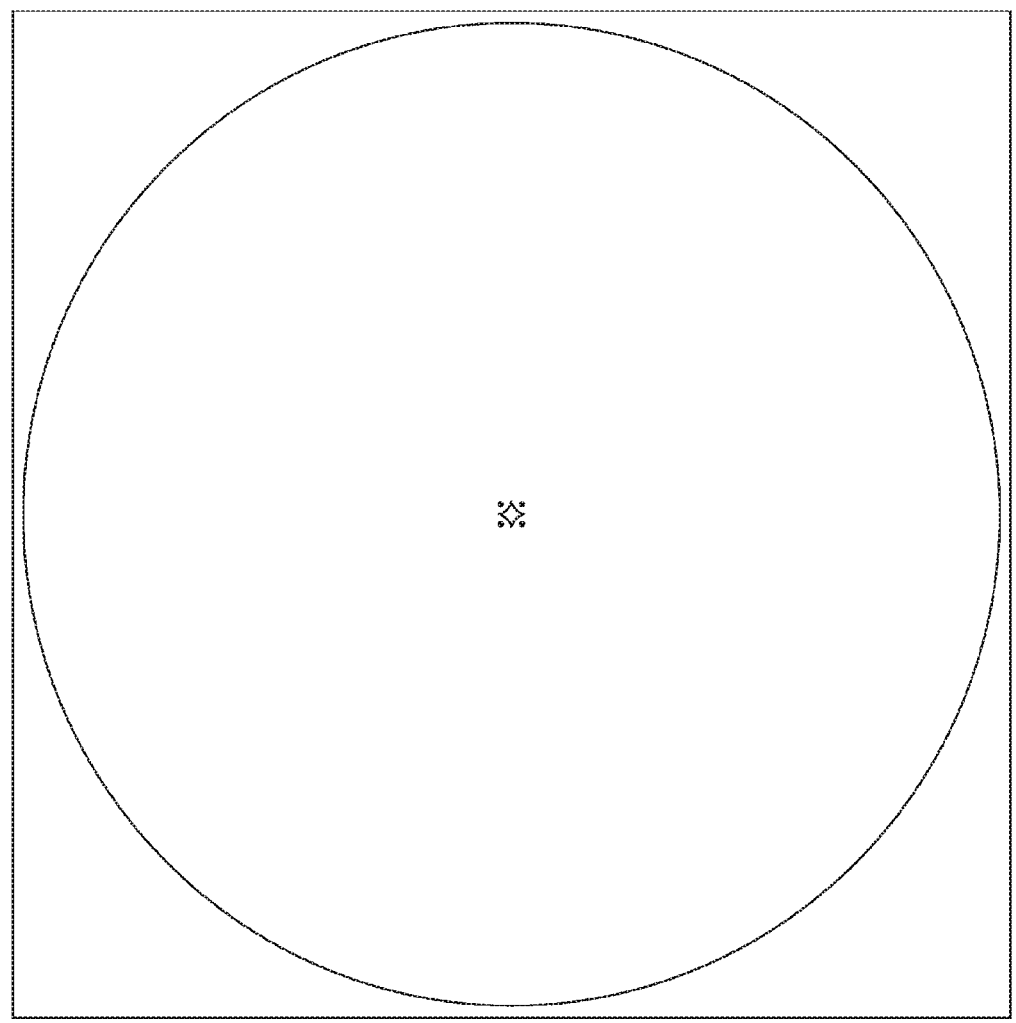
FIG. 3 is a schematic view of a sound pressure distribution of an ultrasonic wave when a full aperture of a ring array R according to the embodiment of the present invention is used.

FIG. 3 schematically illustrates a waveform of ultrasonic waves when the full aperture of the ring array R is used. Ultrasonic waves transmitted from the elements disposed at even intervals cancel out each other and converge at a central point. By using data corresponding to the full aperture of the ring array R, movements of the subject T in any directions can be therefore detected, as well as an image with higher resolution can be captured and created because of a narrower width of a point response function.

The operational circuit 130 captures and creates an image using Doppler signals received by the elements. Specifically, the operational circuit 130 cross-correlates signals between packets to calculate an amount of change in blood to measure a flow amount. When a flow amount is to be calculated, a slow component corresponding to a body motion velocity is removed from a detection velocity in a packet, which is acquired from the cross-correlated signals between the packets. A magnitude of a cross-correlation value acquired by cutting the slow component is regarded as a flow amount in a subject location and its spatial distribution is imaged.

For a flow amount, sufficiently beneficial information can be acquired even if no information on a flow direction is included. The operational circuit 130 can therefore present an image by combining the measured flow amount and an estimation result on a flow velocity, described later. An example of image presentation method may be filtering an output in proportion to a magnitude of a flow amount so as not to display components with a less flow amount. When a filter having an output proportional to a magnitude of a flow amount is to be applied to a result of measurement on a flow velocity, aperture conditions appropriate for respective flow velocity measurements and flow amount measurements can be used to alternately perform measurements. In a flow amount measurement, by expanding an aperture as much as possible, in other words, by setting expanding distribution of elements to be used for transmission or reception as wide as possible, a higher spatial resolution can be achieved. On the other hand, as will be described later in detail, in a flow velocity measurement, measurements will be performed per vector component. Anisotropy is thus required in a spatial distribution in transmission/reception sensitivity, i.e., in a point response function. It is therefore advantageous that an aperture be limited, in other words, the width of element distribution used for transmission or reception are distributed be limited. As a result, a collection of elements used for a flow velocity measurement is a part of a collection of elements used for a flow amount measurement. The number of elements used in a flow velocity measurement is otherwise lesser than the number of elements used in a flow amount measurement. This does not mean that this condition is always achieved in both transmission and reception, but means that, in either transmission or reception, the number of elements used in a flow amount measurement and the number of elements used in a flow velocity measurement satisfy a size relationship or a relationship of set and subset.

By using the full aperture of the ring array R, movements in any directions can be detected. However, a fact that movements in any directions can be detected means that a direction of a blood flow cannot be identified in an observation portion of the subject T. In the ultrasonic diagnostic system 10 according to the embodiment, when a flow velocity is to be measured, the aperture is therefore limited for measurement.

Blood Flow Velocity Measurement Process

Next, a blood flow velocity measurement process will now be described herein. A conventional device that measures a velocity vector using a Doppler signal can only detect a movement in a direction in which ultrasonic waves propagate, among velocity components of blood flows. To solve this problem, the ultrasonic diagnostic system 10 according to the embodiment is configured to be able to analyze Doppler signals reflected in two different directions, to measure and compound velocity vectors in respective directions, and to calculate a blood flow velocity. The embodiment describes that Doppler signals in two directions perpendicular to each other are analyzed. However, as long as Doppler signals having reflection angles different from each other are used for analysis, Doppler signals having reflection angles perpendicular to each other may not be necessary.

Methods for controlling elements to transmit and receive ultrasonic waves in a flow velocity measurement process may include methods according to first and second configurations respectively, for example.

1. First Configuration

Figure 4A:
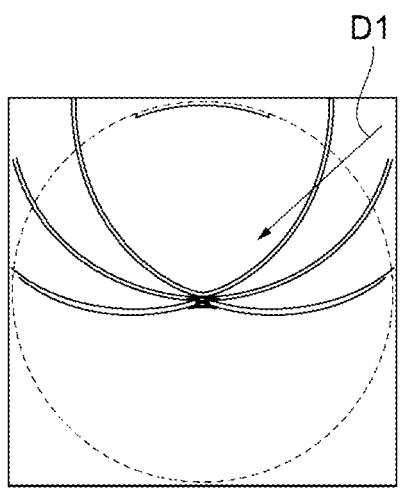
FIGS. 4A and 4B show schematic views of transmission and reception of ultrasonic waves in a first configuration according to the embodiment of the present invention.
Figure 4B:
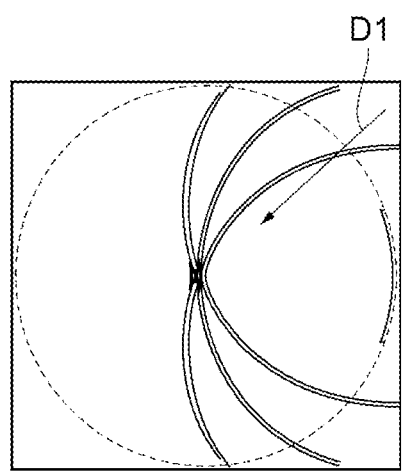

FIGS. 4A and 4B schematically illustrate how ultrasonic waves are transmitted and received in a first configuration. In the first configuration, the ultrasonic diagnostic system 10 transmits ultrasonic waves in a direction D1 inclined at an angle of 45 degrees (which is an example first angle), and receives Doppler signals in two directions to each other, i.e., the two directions respectively inclined at angles of 0 degrees (which is an example second angle) and 90 degrees (which is an example third angle) from the central axis. In here, an angle refers to an angle between a vector formed by connecting a center of a transmission aperture and a focal point for transmission and a predefined reference line (e.g., a straight line formed by connecting a position between the elements e0 and e1024 and a center of a circle).

FIG. 4A is a view schematically illustrating how ultrasonic waves are transmitted in the direction D1 inclined at an angle of 45 degrees and how Doppler signals are received in the direction at the central axis angle of 0 degrees. FIG. 4B is a view schematically illustrating how ultrasonic waves are transmitted in the direction D1 inclined at an angle of 45 degrees and how Doppler signals are received in the direction at the central axis angle of 90 degrees.

Figure 5:
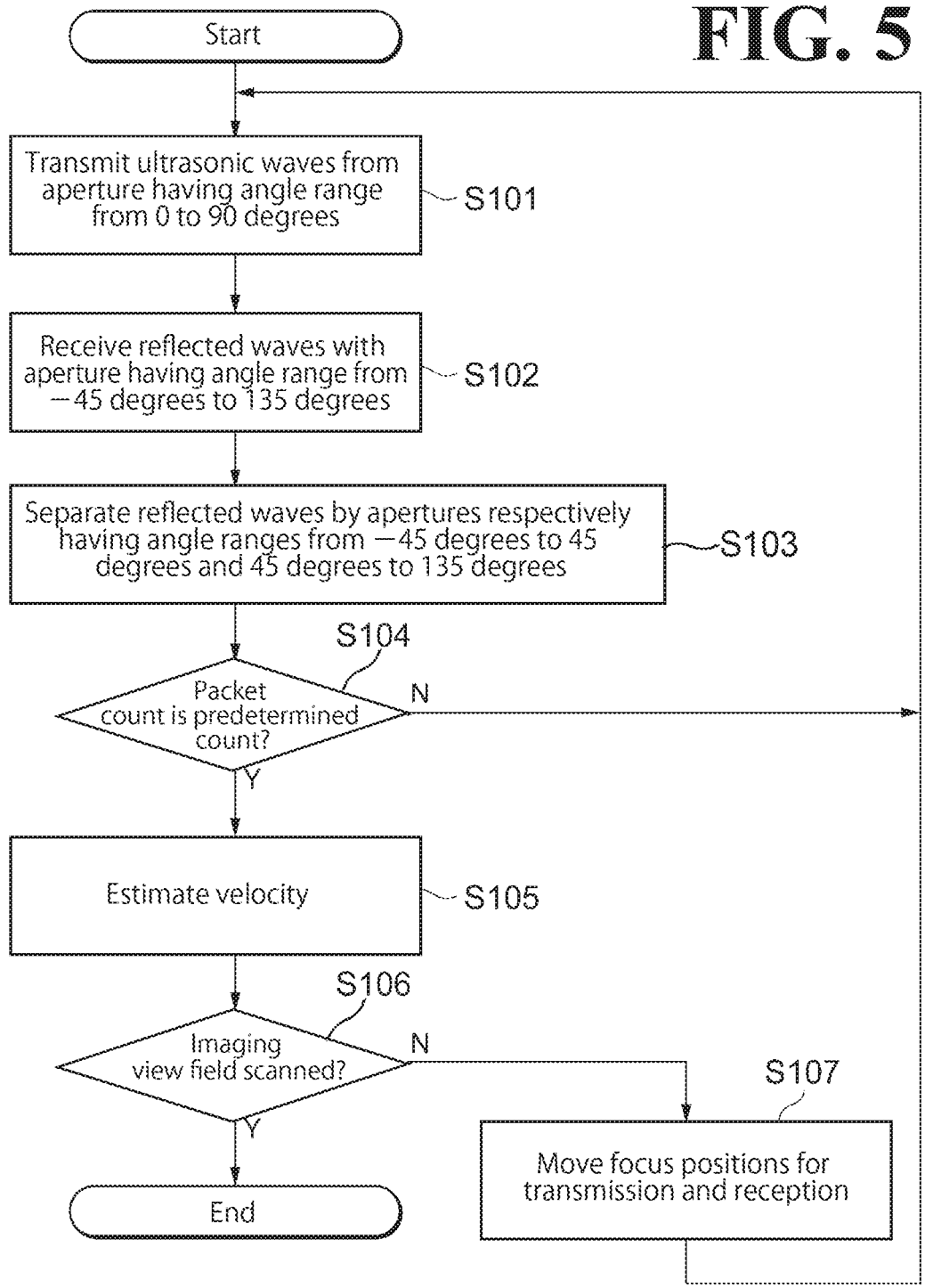
FIG. 5 is a flowchart of a blood flow velocity measurement process in the first configuration according to the embodiment of the present invention.

An example process flow performed by the ultrasonic diagnostic system 10 in the first configuration will now be described herein with reference to FIG. 5.

The transmission/reception circuit 120 generates, in number corresponding to a packet count, control signals for transmitting and receiving ultrasonic waves at a predetermined frequency. The switch 110 sequentially conveys control signals to drive the elements e1 to 256 respectively disposed at angles ranging from 0 to 90 degrees so that ultrasonic waves transmitted from the elements simultaneously reach a center of the insertion portion SP. For example, to allow ultrasonic waves to focus at a geometrical center position, delay times for the elements e1 to e256 are all set to 0 to convey control signals. In an order with which the control signals are provided, driven elements sequentially transmit ultrasonic waves (S101).

Next, the switch 110 conveys the control signals to the elements e896 to e1024 and the elements e1 to e384 respectively disposed at angles ranging from −45 degrees to 135 degrees to cause the elements to sequentially repeat transmissions and receptions so as to receive Doppler signals (S102). The Doppler signals are separated into two groups for signal processing: the Doppler signals received by the elements e896 to e1024 and the elements e1 to e128 respectively disposed at angles ranging from −45 degrees to 45 degrees and the Doppler signals received by the elements e129 to e384 respectively disposed at angles ranging from 45 degrees to 135 degrees (S103). The term "separation" in here denotes that signal processing for a particular element group and signal processing for another element group are separated and calculated in parallel. In the embodiment, signal processing for the elements e896 to e1024 and the elements e1 to e128 and signal processing for the elements e129 to e384 are fully separated and calculated in parallel.

The processing of S101 to S103 are repeated until the switch 110 finishes conveying the control signals to the number corresponding to the packet count generated by the transmission/reception circuit 120 to the elements (S104: YES). Upon the reception data of the predetermined packet count (in the embodiment, eight packets) is collected, the operational circuit 130 performs a flow velocity calculation process, which will be described later, to extract a phase change, and calculates velocity vectors at angles of 0 and 90 degrees. The operational circuit 130 compounds the calculated velocity vectors at the angles of 0 and 90 degrees to estimate blood flow velocities (S105).

If the imaging view field is not fully scanned (S106: NO), a distribution of delay times to be applied to the elements is changed to move focus positions at which the elements transmit and receive ultrasonic waves (S107). The processing of S101 to S107 are repeated until the imaging view field is fully scanned (S106: YES). To capture a three-dimensional image, the ring array R is further moved up and down to repeat the steps described above.

In the above described control method according to the first configuration, transmission elements and reception elements used in a packet are switched, which may lead to a noise when the switch 110 performs switching. On the other hand, in the control method according to the first configuration, the transmission elements are fixed, and therefore scanning can be performed without sacrificing a frame rate (resolution).

As another applicable example for the control method of Configuration 1, ultrasonic waves are transmitted from a certain aperture (a portion that performs transmission and reception in the array), and the ultrasonic waves are received with a different aperture, then another ultrasonic waves are transmitted from an aperture different from the initial transmission, and then it received by the same aperture as the initial reception. For example, ultrasonic waves are transmitted at an aperture from –45 degrees to 45 degrees, received at an aperture of 0 to 90 degrees, then transmitted at an aperture of 45 degrees to 135 degrees, and again received at the aperture of 0 to 90 degrees. The exemplary method may alternately repeat this process. In this case, a single reception aperture is always used, and accordingly, before one transmission waveform is fully acquired, the other ultrasonic wave can be transmitted under other transmission condition. Therefore, an image can be captured promptly. An image can be captured further promptly by setting apertures for transmission elements and reception elements so that the transmission elements and the reception elements do not overlap. This method can be realized, for example, by transmitting ultrasonic waves from an aperture having an angle range from 30 to 60 degrees, receiving the ultrasonic waves by an aperture from 60 to 120 degrees, then transmitting another ultrasonic wave from an aperture from the angle range from 60 to 120 degrees again.

FIGS. 9A to 9D show photos illustrating difference in results of calculations of spatial distributions in sensitivity according to a difference between reception apertures on transmission and reception of Doppler signals.

FIGS. 9A and 9B are photos each illustrating a spatial distribution (point response function) in sensitivity when ultrasonic waves are transmitted in the direction D1 of 45 degrees, and Doppler signals are respectively received in atwo directions at the central axis angles of 0 degrees (FIG. 9A) and 90 degrees (FIG. 9B). In this case, an angle formed by a difference in inclinations of the point response functions illustrated in FIGS. 9A and 9B does not reach 90 degrees.

On the other hand, FIGS. 9C and 9D are photos each illustrating a spatial distribution (point response function) in sensitivity when ultrasonic waves are transmitted in the direction D1 inclined at an angle of 45 degrees, and Doppler signals are received in two directions respectively perpendicular to the direction D1, i.e., the two directions respectively having central axis at an angle of 135 degrees (FIG. 9C) and –45 degrees (FIG. 9D). In this case, an angle formed by a difference in inclinations of the point response functions illustrated in FIGS. 9C and 9D is expanded to 90 degrees. Velocity vectors of blood flows in all directions can therefore be captured in an image. As exemplified above, it is advantageous that a reception position be set so as to allow a difference in inclinations of point response functions to form an angle of 90 degrees.

In a conventional Doppler imaging method, a direction toward which ultrasonic waves propagate and a direction used in a time sampling method for an analog-digital converter match each other. In the present invention, echo signals transmitted or received in a plurality of different propagation directions are compounded in a state where a direction of time axis sampling and each of the propagation directions differ, and thus its cross-correlation makes it difficult to define a velocity on a time axis. To solve this problem, in the present invention, it is advantageous that a unique direction of a time axis be set per observation point, and acquired reception echo data be rearranged by taking into account positions of transmission and reception elements so as to arrange the data on the time axis.

2. Second Configuration

Figure 6A:
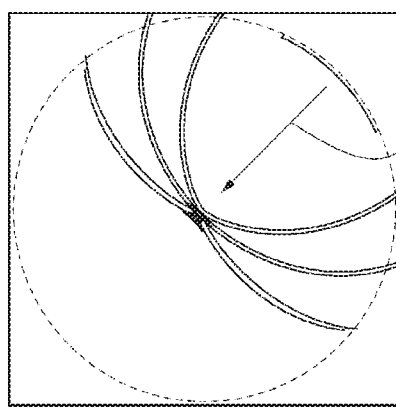
FIGS. 6A and 6B show schematic views of transmission and reception of ultrasonic waves in a second configuration according to the embodiment of the present invention.
Figure 6B:
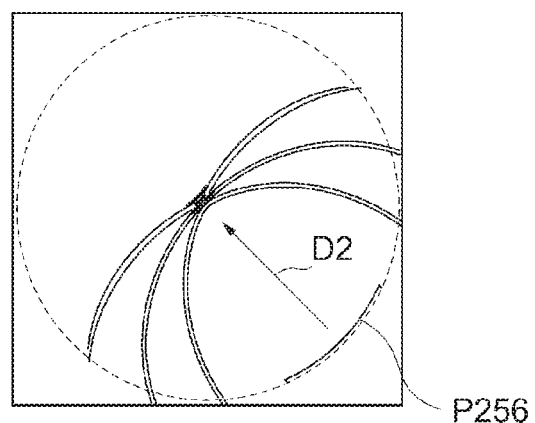

FIGS. 6A and 6B schematically illustrate example transmissions and receptions of ultrasonic waves in a second configuration. In the second configuration, for example, the ultrasonic diagnostic system 10 transmits and receives ultrasonic waves in the direction D1 inclined at an angle of 45 degrees, and then transmits and receives ultrasonic waves in a direction D2 inclined at an angle of 135 degrees. FIG. 6A is a view schematically illustrating how ultrasonic waves are transmitted in the direction D1 inclined at an angle of 45 degrees, and how Doppler signals are received at a central axis angle of 45 degrees. FIG. 6B is a view schematically illustrating how ultrasonic waves are transmitted in the direction D2 inclined at the angle of 135 degrees, and how Doppler signals are received in a direction inclined at a central axis angle of 135 degrees.

Figure 7:
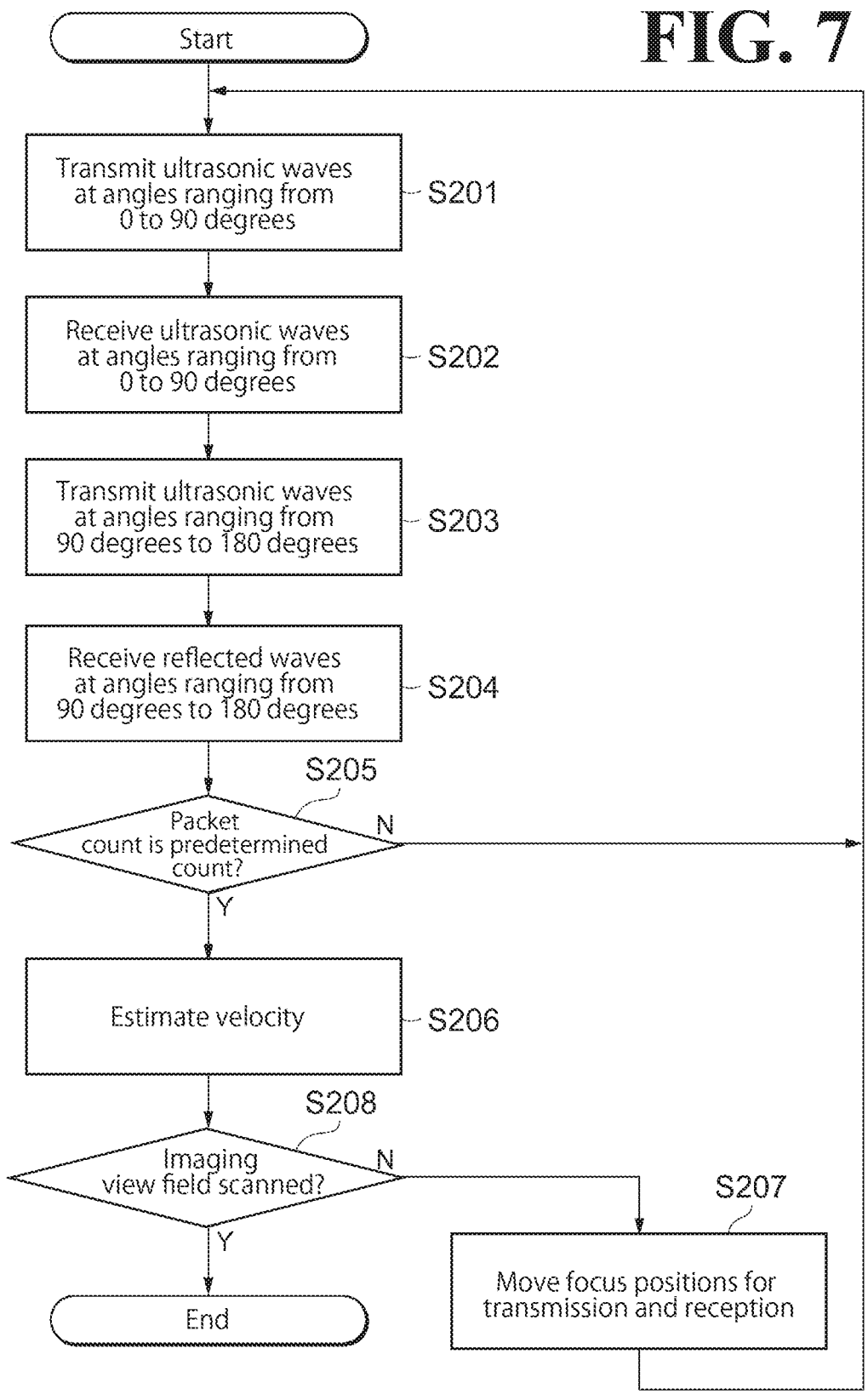
FIG. 7 is a flowchart of a blood flow velocity measurement process in the second configuration according to the embodiment of the present invention.

An example process flow performed by the ultrasonic diagnostic system 10 in the second configuration will now be described herein with reference to FIG. 7.

The transmission/reception circuit 120 generates, in number corresponding to a packet count, control signals for transmitting and receiving ultrasonic waves at a predetermined frequency. The switch 110 sequentially conveys the control signals to drive the elements e1 to 256 respectively disposed at angles ranging from 0 to 90 degrees so that ultrasonic waves transmitted from the elements simultaneously reach the center of the insertion portion SP. Specifically, a delay time set based on a value acquired by dividing a distance from a transmission focus position to an element position with an estimated sound velocity is used to convey the control signals. In an order with which the control signals are provided, driven elements sequentially transmit ultrasonic waves (S201). The switch 110 further conveys a control signal to the elements e1 to 256 respectively disposed at the angles ranging from 0 to 90 degrees to cause the elements to receive Doppler signals (S202).

Upon the reception of the Doppler signals completes, the switch 110 sequentially conveys the control signals to drive the elements e257 to 512 respectively disposed at angles ranging from 90 to 180 degrees so that ultrasonic waves transmitted from the elements simultaneously reach the center of the insertion portion SP. Specifically, a delay time set based on a value acquired by dividing a distance from a transmission focus position to an element position with an estimated sound velocity is used to convey the control signals. In an order with which the control signals are provided, driven elements sequentially transmit ultrasonic waves (S203). The switch 110 further convey the control signals to the elements e257 to 512 respectively disposed at the angles ranging from 90 to 180 degrees to cause the elements to receive Doppler signals (S204).

The processing of S201 to S204 are repeated until the switch 110 finishes conveying the control signals to the number corresponding to the packet count generated by the transmission/reception circuit 120 to the elements (S205: YES).

Upon the reception data of the predetermined packet count (in the embodiment, eight packets) is collected, the operational circuit 130 performs a flow velocity calculation process, described later, to extract a phase change to calculate velocity vectors at angles of 45 degrees and 135 degrees. The operational circuit 130 compounds the calculated velocity vectors at the angles of 45 degrees and 135 degrees to estimate a blood flow velocity (S206). If the imaging view field is not fully scanned (S208: NO), the ring array R is moved up and down to move focus positions at which the elements transmit and receive ultrasonic waves (S207). S201 to S208 are repeated until the imaging view field is fully scanned (S208: YES).

In the above described control method according to the second configuration, transmission elements and reception elements used are not switched within a packet, which may reduce the occurrence of noise due to a switch processing. On the other hand, required switching of the transmission elements and performing of transmissions twice may lower a frame rate (resolution) in a captured image.

In the above described case, apertures are narrowed for both transmission and reception by limiting both elements used to transmit and receive ultrasonic waves to achieve an appropriate focus. However, another applicable method is a high-speed imaging method in which no beam (aperture) in transmitting ultrasonic waves is narrowed in transmitting ultrasonic waves, but a plurality of different locations are focused simultaneously in receiving ultrasonic waves. For example, by increasing a width of a transmission beam approximately ten times of a width of a reception beam, and forming ten reception beams within the width, a total imaging time can be reduced by ten times. More specifically, since a width of a transmission beam and a width of a reception beam respectively are in reverse proportion to a width of an aperture, the number of elements used for transmission may be reduced to one tenth of the number of elements used for reception to increase a width of a transmission beam ten times a width of a reception beam. In Doppler imaging, an increase in speed of imaging allows designing of a body motion removal filter with sharper cut-off capability, achieving rendering of a flow of blood flowing at a slow velocity that is approximately identical to a velocity of a body motion.

In 1. and 2. above, the specific configuration examples are described. However, the present invention, which is capable of calculating a velocity vector by performing vector composition by using Doppler signals respectively received by elements positioned at different angles relative to a subject, may also be configured as described below. That is, the present invention provides an ultrasonic diagnostic system including a plurality of elements, a controller, and an operator. The plurality of elements is disposed around a subject, and is configured to transmit and/or receive ultrasonic waves. The controller is configured to control the plurality of elements so that elements configuring a part of the plurality of elements transmit ultrasonic waves toward a diagnosis target in the subject, and reflected waves of the ultrasonic waves, which are reflected from the diagnosis target, are received by two or more elements disposed in regions where angles of reflection from the diagnosis target differ from each other. The operator is configured to calculate a velocity vector of the diagnosis target using the reflected waves respectively received by the two or more elements. An example of a specific system control method may be identical to the above described 1. or 2.

The present invention, which is capable of radiating ultrasonic waves from elements disposed at two locations toward a subject, of receiving reflected waves of the ultrasonic waves by the elements disposed at the two locations, of performing vector composition using Doppler signals respectively received by the elements disposed at the two locations, and of calculating a velocity vector, may be configured as described below. That is, the present invention provides an ultrasonic diagnostic system including a plurality of elements, a controller, and an operator. The areplurality of elements is disposed around a subject, and is configured to transmit and/or receive ultrasonic waves. The controller is configured to control the plurality of elements so that elements disposed in a first region, among the plurality of elements, transmit first ultrasonic waves toward a diagnosis target in the subject, the elements disposed in the first region receive reflected waves of the first ultrasonic waves, which are reflected from the diagnosis target, elements disposed in a second region, among the plurality of elements, transmit second ultrasonic waves toward the diagnosis target, and the elements disposed in the second region receive reflected waves of the second ultrasonic waves, which are reflected from the diagnosis target. The operator is configured to calculate a velocity vector of the diagnosis target using the reflected waves of the first and second ultrasonic waves. An example of a specific system control method may be identical to the above described 1. or 2.

3. Flow Velocity Calculation Process

Next, a flow velocity calculation process performed by the operational circuit 130 will now be described herein.

Figure 8A:
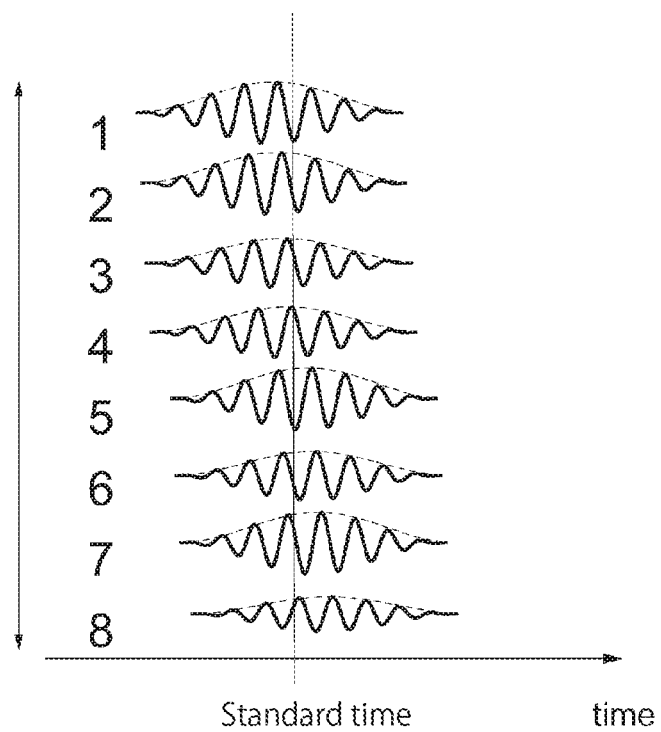
FIGS. 8A and 8B show graphs indicative of relationships between Doppler signals received with packets and blood flow velocities, according to the embodiment of the present invention.

The operational circuit 130 uses received Doppler signals to analyze a velocity vector of a blood flow. FIG. 8A illustrates waveforms of Doppler signals corresponding to eight packets received by reception elements. A horizontal axis of the graph illustrated in FIG. 8A shows a relative elapsed time after elements have transmitted ultrasonic waves in each of the packets. In the graph illustrated in FIG. 8B, amplitudes of the Doppler signals corresponding to the packets shown in FIG. 8A in a standard time are plotted.

Since a sound can be represented in a waveform of a sine function, a change in phase in the standard time among the packets (an inclination of the graph illustrated in FIG. 8B) represents a velocity of a blood flow.

Figure 8B:
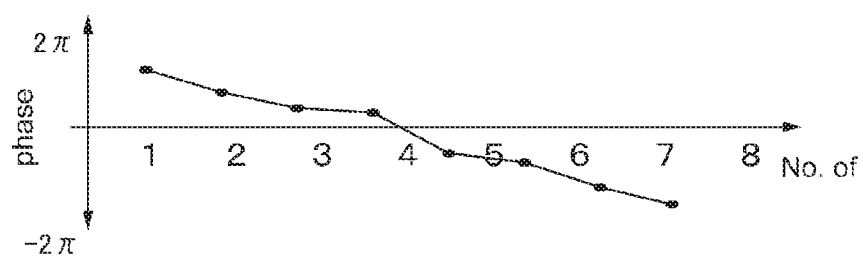

The operational circuit 130 uses a velocity calculated from the graph illustrated in FIG. 8B and directions from which the elements have received the Doppler signals to calculate a velocity vector per each of the directions from which the elements have received the Doppler signals. By compounding the calculated velocity vectors, velocity vectors of blood flows can be estimated.

As described above, the ultrasonic diagnostic system 10 according to the embodiment can measure a flow velocity regardless of which direction blood flows.

One of major benefits of the present invention is, when a blood flow can be measured with a vector, a novel body motion removal filter, described later in detail, can be constructed to achieve a visualized distribution of slow blood flows. Visualizing of slow blood flows leads to a higher possibility of rendering new tumor blood vessels around a tumor, improving tumor detection sensitivity and increasing information used to judge the tumor.

In a conventional Doppler method with which only a velocity component in a direction in which ultrasonic waves propagate is detected, a velocity range filter is used to separate blood flows and a movement of body tissue due to breathing and beating, for example. In the conventional method, a movement at a velocity below a threshold is regarded as a body motion, and thus is removed from a blood flow signal, while only a movement at a velocity above the threshold is indicated as a blood flow signal. In the above described conventional method, therefore, blood flow components at a velocity below a set threshold are all removed. On the other hand, the ultrasonic diagnostic system 10 according to the example keeps a vector component as a signal, and therefore, even when a body motion and a slow blood flow have identical velocities, as long as they move in a direction different from each other, the body motion and the slow blood flow can be separated.

Figure 10:
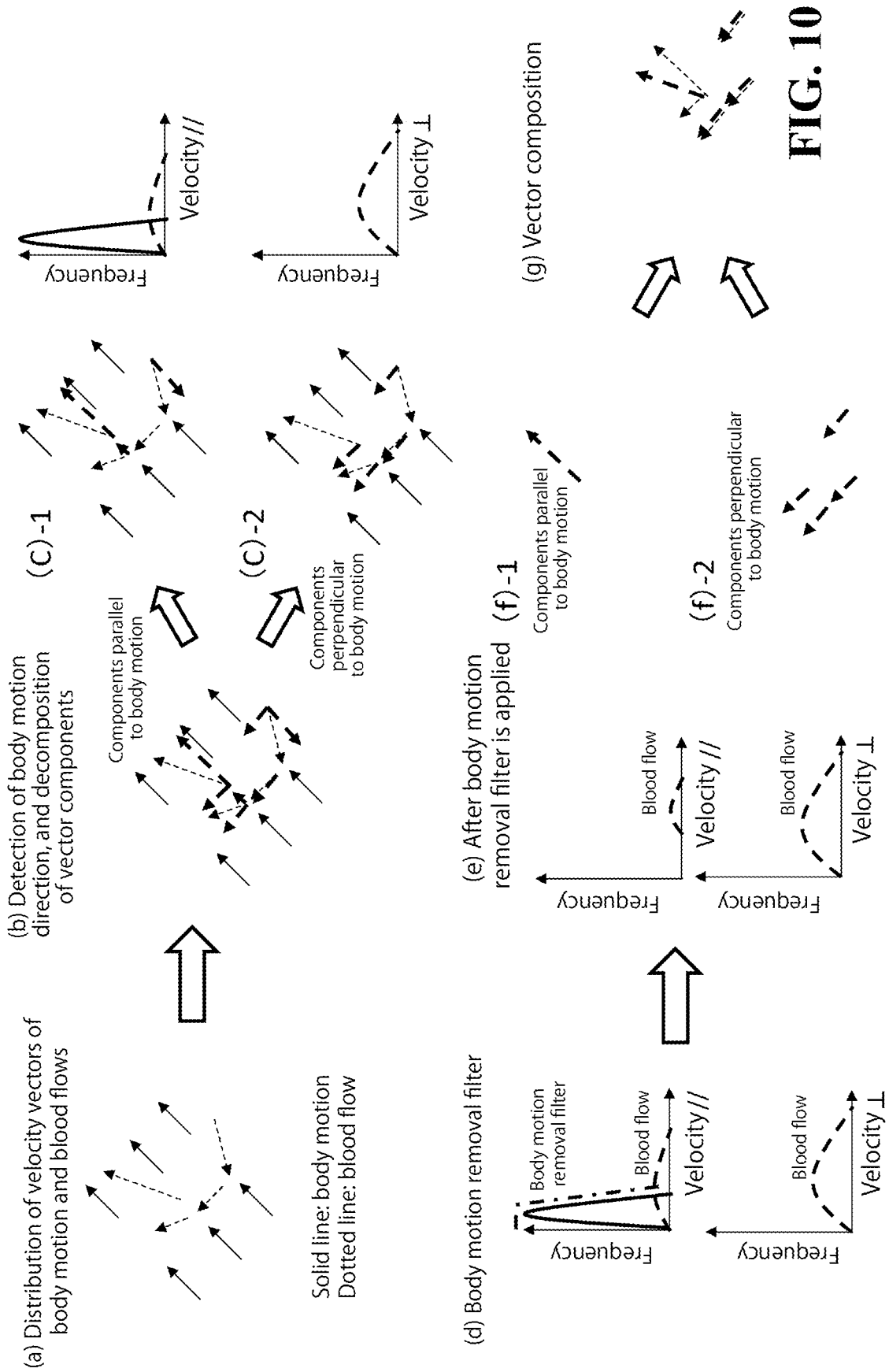
FIG. 10 shows schematic views of a process of separating and retrieving slow blood flows in directions different from a direction of a body motion, according to the embodiment of the present invention.

FIG. 10 shows schematic views of a process of separating slow blood flows and a body motion to retrieving only the slow blood flows. In FIG. 10, solid line arrows represent velocity vectors of a body motion, while dotted line arrows represent velocity vectors of slow blood flows.

FIG. 10(a) illustrates a distribution of velocity vectors of a body motion and blood flows. The operational circuit 130 detects a direction of the body motion from the velocity vectors of the body motion. Next, the operational circuit 130 decompounds the velocity vectors of the blood flows into components parallel to the direction of the detected body motion and components perpendicular thereto (FIGS. 10(b), (c)-1, and (c)-2). From the components parallel to the direction of the body motion among decompounded components of velocity vectors of slow blood flows, velocity vectors of the slow blood flow falling within a velocity range in which the body motion component is present are removed (FIGS. 10(d) and (e)).

FIG. 10(f) illustrates a state in which the vectors related to the blood flows are distributed again after removing the slow blood flows having velocities that are identical to the velocity of the body motion. FIG. 10(f)-1 illustrates the component parallel to the body motion, while FIG. 10(f)-2 illustrates components perpendicular to the body motion. By compounding the components illustrated in (f)-1 and (f)-2 in FIG. 10, velocity vectors of slow blood flows, from which the body motion is removed, can be acquired (FIG. 10(g)). As described above, the ultrasonic diagnostic system 10 according to the embodiment can separate and handle a body motion and slow blood flows when vectors of the body motion and the slow blood flows face different directions. In addition, the ultrasonic diagnostic system 10 according to the embodiment does not filter slow-blood flow-directing components in a different direction from the body movement, and thus it can store more slow blood flow signals.

A method for setting a velocity cut-off value to remove a body motion can be achieved as described below. As illustrated in FIG. 10(a), a body motion has same vectors acting across a wide range, while a blood flow has vectors that differs per location. In particular, a slow blood flow, which is discussed in here, is a flow of blood that flows into a narrower blood vessel, and thus that has a velocity vector that changes greatly per location as the blood vessel changes its running direction per the location. By utilizing this feature, spatially-common velocity vector components are regarded as a body motion, while a velocity vector component that is less spatially related to other locations is regarded as a blood flow, to set a cut-off value that can effectively separate them.

Figure 11:
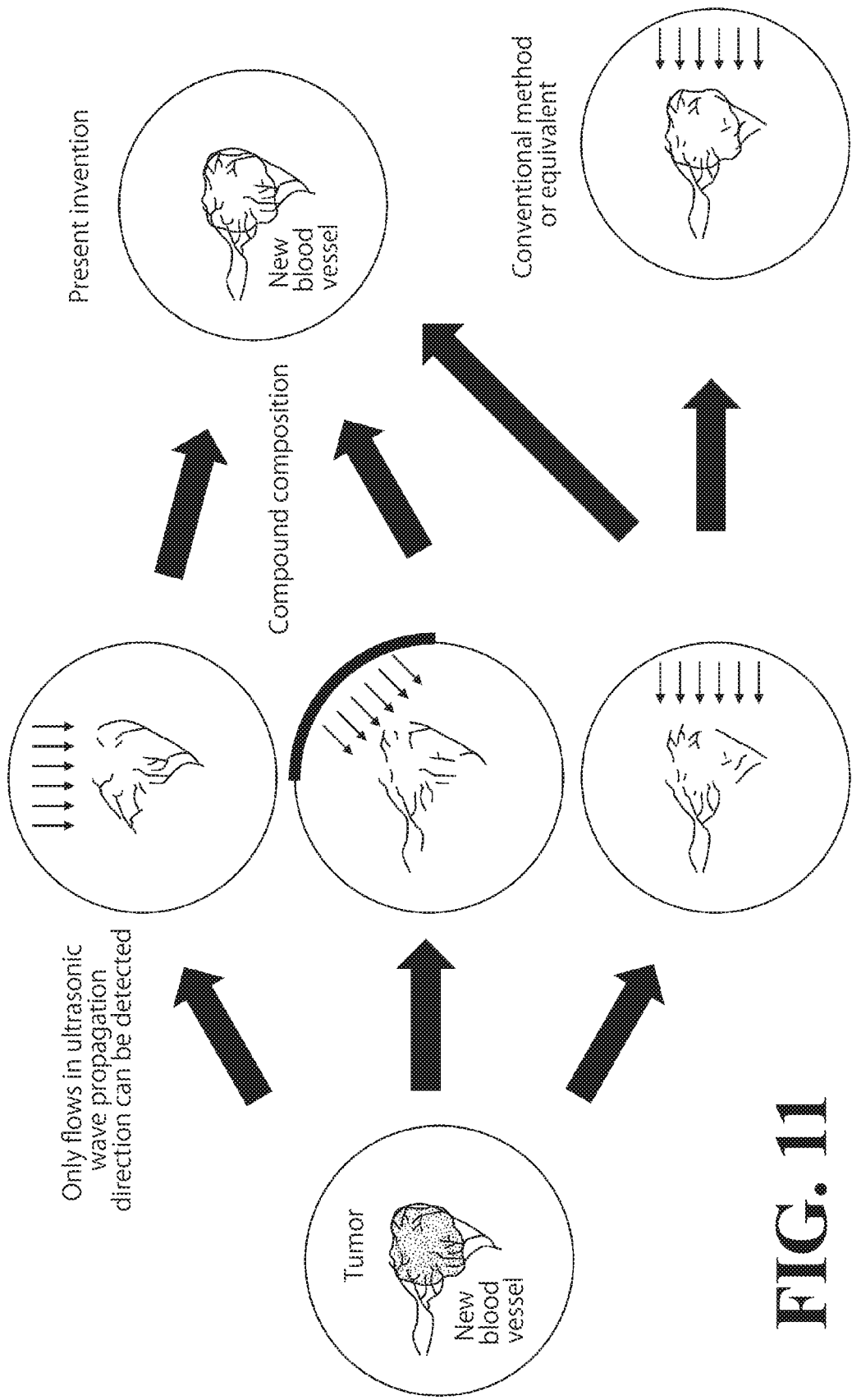
FIG. 11 is a schematic view of a Doppler image compounding process according to the embodiment of the present invention.

FIG. 11 is a schematic view of a Doppler image compounding process As illustrated in FIG. 11, compounding Doppler images captured from multiple directions can prevent such a phenomenon that a structure of a blood vessel is intermittently visualized depending on the blood stream direction, which happen in capturing an image relying on a single direction.

The process illustrated in FIG. 11 is a method developed from a method for performing composition (compounding) of images (e.g., tomographic images) captured by transmitting and receiving ultrasonic waves in a plurality of different directions set so as to surround a target region to be imaged in ordinary ultrasonic wave tomographic imaging. Compounding images in tomographic imaging can reduce effects of angular dependency in reflection ratios of boundary faces and scatterers present in an object.

4. Another Body Motion Removal Method (Singular Value Decomposition)

In the above 1. to 3., examples each including a step of estimating velocities in two directions, and a step of separating a body motion and blood flows per velocity component to remove the body motion are described. A method for removing a body motion by simultaneously using pieces of information on two directions from movements including a body motion and blood flows will now be described hereunder.

How to change a control method for acquiring signals to increase flexibility in signal processing will now first be described herein. In the above 1. to 3., the examples have used a method in which an imaging region is spatially divided, ultrasonic waves are focused on each of the divided regions and transmitted (S107 in FIG. 5 and S207 in FIG. 7), and then transmitting and receiving ultrasonic waves are repeated toward and from a predetermined transmission focal point until a predetermined packet count (approximately eight to ten: S104 in FIG. 5 and S205 in FIG. 7) is satisfied. As for dynamic imaging of a spatial distribution of blood flows, an imaging velocity is approximately in reverse proportion to a product of a spatial division count (the number of focus positions for transmission) and a packet count (The term "approximately" implies that there may be a case where packets under different transmission conditions can be inserted between one another. In this case, a measurement can be performed at an imaging rate greater than an inverse number of a product of a spatial division count and a packet count).

Increasing a packet count usually improves flexibility in designing a signal processing method. One method for increasing a packet count without changing a total imaging time is to reduce a spatial division count. A reduction in both the numbers of focus points for transmission and reception leads to a reduced spatial resolution. However, as for a reception focal point, signal processing on a plurality of different focus positions for reception can be performed in parallel. Thus, a packet count can be increased by expanding a region into which a transmission beam focuses to reduce a spatial division count with respect to a transmission focus, while keeping a spatial division count with respect to a reception focus maintained. Specifically, for a packet count, a value ranging approximately 64 to 512 is used, for example. In this process, the control flows in FIGS. 5 and 7 without the processing of S107 and S207 respectively removed are applied.

By increasing a packet count as described above and combining two dimensions of space and one dimension of time, acquired may be a total of three-dimensional data including a component of body motion and components of blood flows in a body tissue. The body motion removal method according to the present invention performs a matrix operation on the acquired three-dimensional data to separate a feature of the body motion and features of the blood flows to remove only the component of the body motion. There are various matrix operation methods that are aimed to process two-dimensional matrices. To utilize such conventional knowledge, it is advantageous that total of three-dimensional data be compressed to two-dimensional data.

A method for compressing the two kinds of three-dimensional data described above to a single two-dimensional data will now be described herein with reference to FIG. 12. The above described three-dimensional data in total in which two dimensions of space and one dimension of time are combined consists of vector information on components in two directions. In other words, it is required that two kinds of three-dimensional data be compressed to a single two-dimensional data. As an example first step for this purpose, as illustrated in FIG. 12, a method called Casorati matrix (for details, see IEEE Trans. Ultrason. Ferr. Freq. Contrl., vol. 34 No. 11 pp. 2271-2285, 2015.) is used. When a propagation direction of ultrasonic waves is specified to a direction x, for example, a pixel space xy is divided into columns in the direction x and rearranged one by one to convert the data into one-dimensional data of xy row×1 column. Then, a two-dimensional matrix is configured with the newly-formed one dimension of space in which the space xy is contracted and one dimension of time. Here, the space is converted into one dimension in order to make tracking of a time-change component of each pixel easier. Also, the space is divided into columns one by one in the direction x in order to detect a movement in the direction x with higher sensitivity because a spatial gradient of a phase of a point response function in the direction x is steep. (When a space is divided into columns one by one in a direction y, a discontinuous movement is found in a Casorati matrix, which is disadvantageous when performing eigen value decomposition.)

Next, another feature of the present invention, i.e., an operation of combining, into a single matrix, two kinds of Casorati matrices in two arbitrary directions of a direction A ((1) in FIG. 12A) and a direction B ((1) in FIG. 12A) and ((2) in FIG. 12A) respectively, for example, will now be described herein with reference to a plurality of examples.

1. By reducing anisotropy in point response function (FIG. 3), an echo signal is allowed to include movement components in two directions to configure a two-dimensional Casorati matrix of single space versus time.

2. By coupling two two-dimensional Casorati matrices of direction A versus time and direction B versus time in a space dimension direction (a longitudinal direction shown in FIG. 12B), a single Casorati matrix is formed, as illustrated in FIG. 12B. (For an alternative minor arrangement to this method, a rearrangement method in which the direction A and the direction B are alternately arranged may be used instead of arranging the direction A and the direction B at an upper half part and a lower half part, respectively, as illustrated in FIG. 12B, for example.)

For separation of a body motion and blood flows included in a two-dimensional Casorati matrix formed with one of the above described methods, various methods widely used in the field of principal component analysis, such as, for example, singular value decomposition on covariance matrix in Casorati matrix and non-negative matrix factorization, can be applied.

An example in which singular value decomposition on covariance matrix in Casorati matrix is used will now be described herein. The operational circuit 130 creates a plurality of images as time elapses. The operational circuit 130 converts the plurality of created images (three-dimensional data consisting of pixel x, pixel y, and time t) into a two-dimensional matrix (hereinafter also referred to as "data S".) having a pixel component (xy: spatial distribution) in a vertical direction and a time component (t: time distribution) in a horizontal direction. In other words, after converted, data of a single image is represented by a vector of single row.

Next, the operational circuit 130 performs singular value decomposition on the data S to calculate a singular value matrix. The operational circuit 130 uses the calculated singular value matrix to further calculate eigen values $\lambda i$ of covariance matrices SS* and S*S in the data S and then to calculate an eigen vector ui with respect to the eigen value $\lambda i$ of the covariance matrix SS* and an eigen vector vi with respect to the eigen value $\lambda i$ of the covariance matrix S*S. The symbol "S*" represents a transposed matrix of S. At this time, it can be regarded that the eigen vector ui represents a component in a spatial distribution of the data S, while the eigen vector vi represents a time change in the spatial distribution of the data S. In the eigen vectors ui and vi, a respective component with $\lambda i$ having a greater value (i.e., value i=around 1) has characteristics of greater signal strength and higher coherence. The characteristics are similar to features of a signal from body tissue motion. It can therefore be regarded that removing a component with $\lambda i$ having a greater value from the data S enables to remove a signal from body tissue motion. As for a component with $\lambda i$ having a greater value, which will be removed, the range of possible value of i can be set from at least 1 to to a desired value but no less than 1.

In the embodiment, by performing singular value decomposition on a compounded image as illustrated in FIG. 11, a body motion can further effectively be removed.

Figures 12A, 12B:
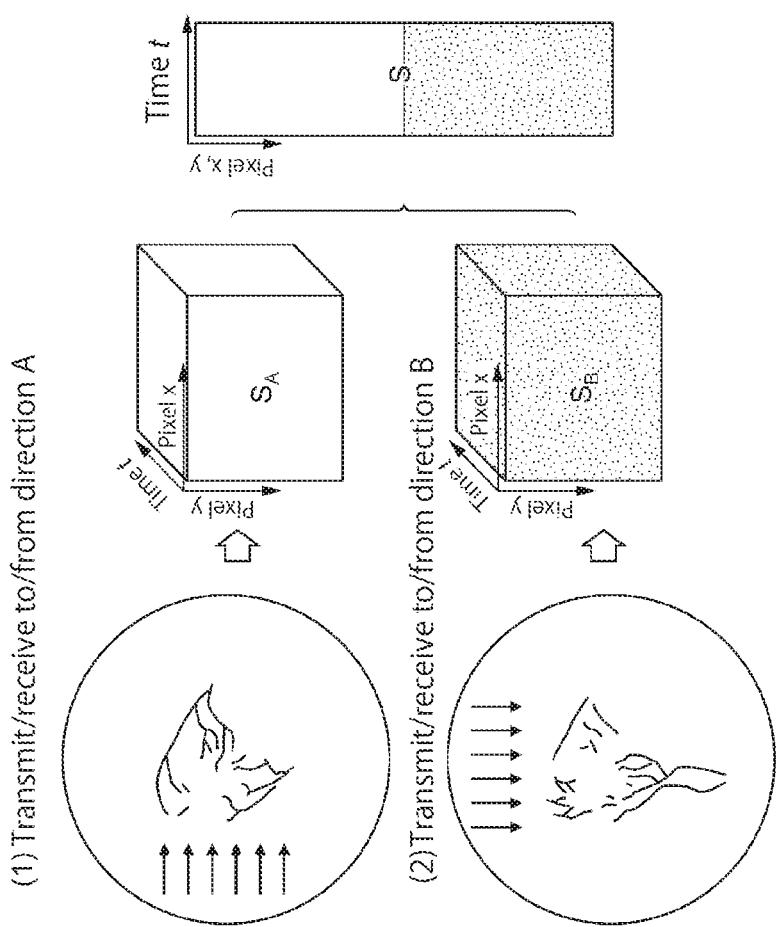
FIGS. 12A and 12B show views of a somatic cell removal filter according to the embodiment of the present invention, the view schematically illustrating an application example.

FIGS. 12A and 12B show schematic views of a body motion removal method according to the embodiment.

FIG. 12A schematically illustrates a plurality of images captured per predetermined time in the direction A, and a plurality of images captured per predetermined time in the direction B. When images are captured in two directions as described above, a body motion component can be removed by performing singular value decomposition on each of the images captured in the two directions.

On the other hand, in the body motion removal method illustrated in FIG. 12, images captured by sequentially transmitting and receiving Doppler signals in a plurality of directions are used to create vector data corresponding to a single column in the data S described above. Specifically, in the example shown in FIG. 12B, an image acquired from Doppler signals transmitted and received in the direction A at a time t ($n_Ax$, $n_Ay$, t) and an image acquired from Doppler signals transmitted and received in the direction B within a predetermined time $\Delta t$ from the time t when the Doppler signals are transmitted and received in the direction A ($n_Bx$, $n_By$, t+$\Delta t$) are regarded as images acquired from signals transmitted and received at an identical time to generate vector data corresponding to a single column in the data S ($n_A x \times n_A y + n_B x \times n_B y$). By generating a plurality of pieces of such the vector data as time elapses, as described above, the data S having a time component formed with a plurality of columns arranged in the horizontal direction is formed. The operational circuit 130 performs singular value decomposition on the matrix data S. Information on a body motion, which cannot be acquired using only an image captured in a single direction, can therefore be acquired, and a body motion component can further effectively be removed.

An example of a bidirectional component has been described. Taking into account features of a ring array, utilizing information on components in three or more directions, as illustrated in FIG. 11, is also beneficial. In particular, when capturing an image of a slow blood flow, an imaging velocity is less restricted, and thus a more number of frames can be acquired. By receiving ultrasonic waves in three or more directions, and rearranging Casorati matrices in the three or more directions into a single Casorati matrix, a process similar to the methods described above can be applied.

Figure 13:
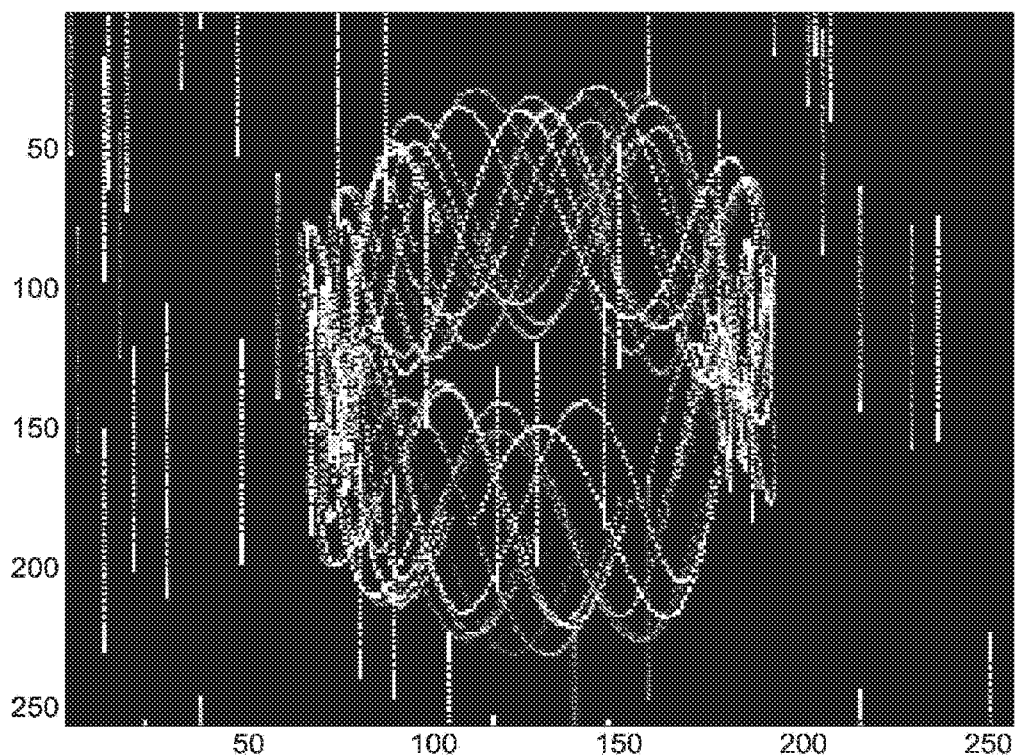
FIG. 13 is a photo of a result when spatial distribution data corresponding to 128 frames in which simulated body motions and simulated blood flows are given to a scatterer distribution is projected in a time direction.
Figure 14:
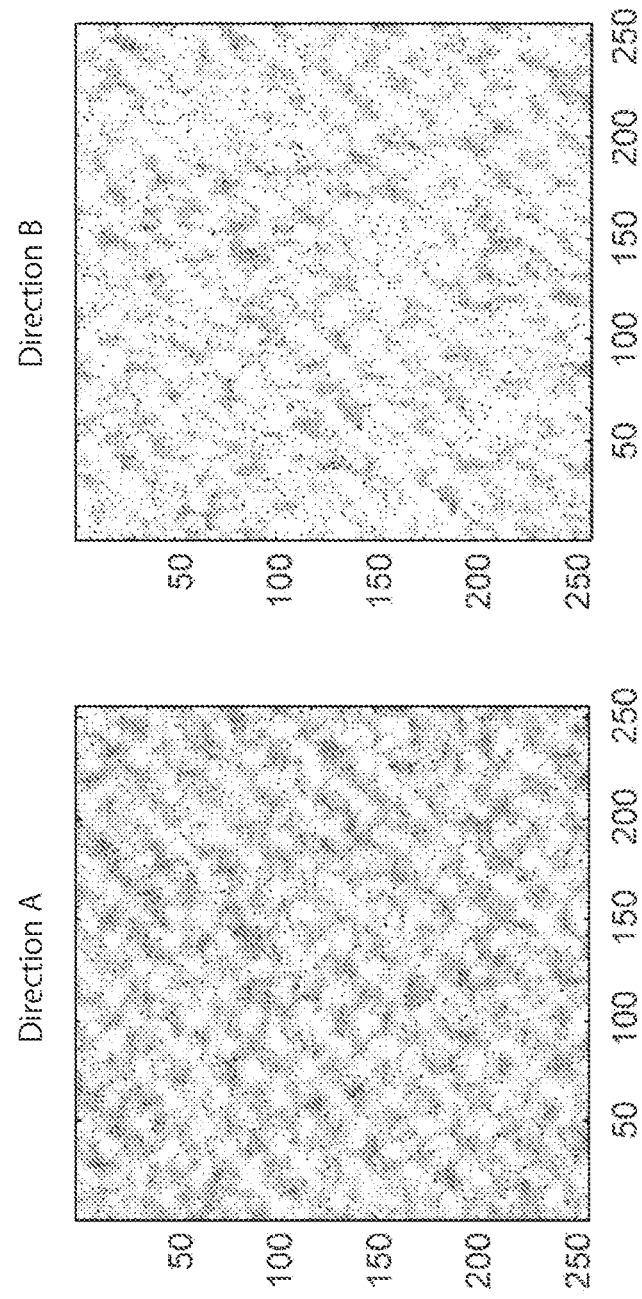
FIG. 14 shows photos of a result after blood flow images are displayed with a method according to a comparative example.
Figure 15:
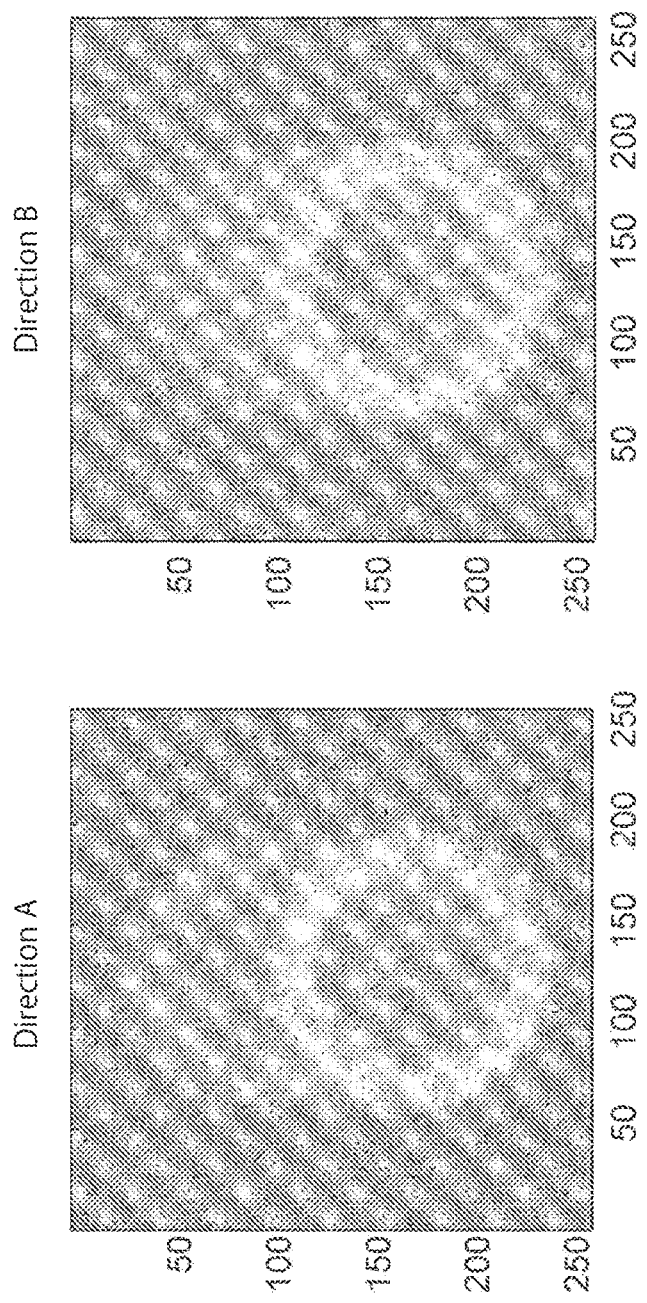
FIG. 15 shows photos of a result after blood flow images are displayed with a method according to a comparative example.

How the method for extracting components of blood flows by removing a body motion from echo components in two directions perpendicular to each other, as described above, is effective will now be described herein with reference to FIGS. 13 to 15 showing specific calculation results. First, for a calculation model, simulated body motions and simulated blood flows are given to a scatterer distribution, and then a two-dimensional convolution operation for point response functions for acquiring ultrasonic echo signals is applied thereto.

The point response functions consist of a point response function corresponding to the direction A and a point response function corresponding to the direction B (a pair of shapes shown in FIGS. 4 and 6 can be acquired for the both functions). FIG. 13 is a photo of a result when spatial distribution data corresponding to 128 frames in which simulated body motions and simulated blood flows are given to a scatterer distribution is projected in a time direction. In here, for description purpose, the number of scatterers for simulating body motions is specified to a value of two to the sixth power, as well as the number of scatterers for simulating blood flows is specified to a value of two to the sixth power, and respective brightness ratios are specified to 1 for visualization. However, in actual calculations described below, the number of scatterers for simulating body motions is specified to a value of two to the twelfth power, as well as the number of scatterers for simulating movements of blood flows is specified to a value of two to the tenth power, so that brightness of blood corpuscles is reduced to one tenth of brightness of body tissue. The simulated blood is allowed to flow in an annular shape in an imaging surface, while the simulated body motion is applied so that the body motion changes in velocity in line with a sine wave in a single direction (128 frames represent one cycle. An amplitude is 40 times a pixel interval in a pixel space.)

FIGS. 14 and 15 illustrate the results of displaying blood flow images through a method according to comparative examples. FIG. 14 illustrates a result when a conventional method wherein a Butterworth filter is applied in a frequency space is used to remove a body motion in the respective directions A and B to display blood flow images. As illustrated in FIG. 14, it can be confirmed that no blood flow information is displayed at all. Next, FIG. 15 illustrates a result when singular value decomposition is performed per direction (in here, the directions A and B), as a method that can easily be conceived from the conventional method. In this result, it can be understood that, although annular blood flows are respectively rendered, the images are significantly affected by the body motion, resulting in heavily blurred circles.

Figure 16:
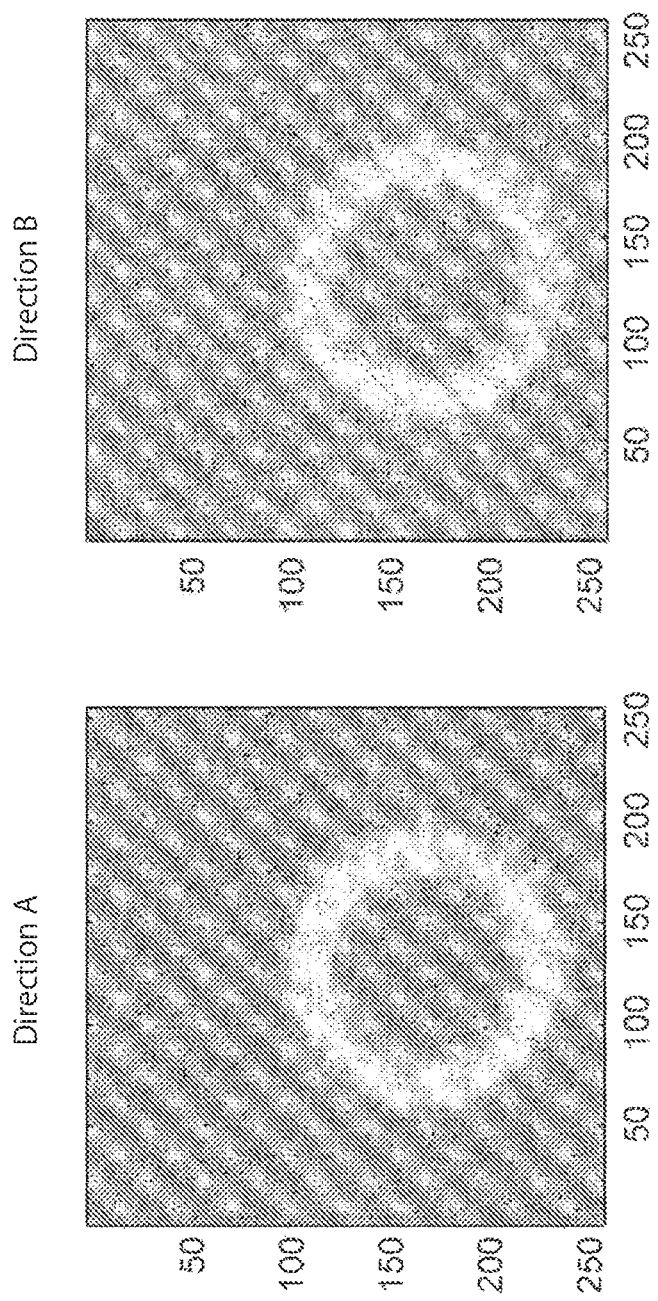
FIG. 16 shows the result of displaying blood flow images through a body motion removal method according to the embodiment of the present invention.

FIG. 16 shows the result of displaying blood flow images through a body motion removal method according to the embodiment. From FIG. 16, it can be confirmed that, with the body motion removal method according to the embodiment, only blood flow signals can be extracted without any blur due to a body motion. Even in the case shown in FIG. 15, if a shape of a spatial distribution of blood flows is known beforehand, the blood flows can be identified from an image blurred by a body motion. In a clinical site, however, it can not know a spatial distribution of blood flows beforehand, and therefore separating true information from a blurred image is difficult. The method illustrated in FIG. 16 is therefore advantageous.

As described above, the body motion removal method described in 3 is a method for calculating a velocity vector by focusing on a point configuring a pixel or one compartment of a separated space. On the other hand, the body motion removal method described in 4 is a method for performing a process which focuses on a spatial distribution of components in two directions by combining two images captured using point response functions of directions different from each other to form a matrix to perform a body motion removal process. The respective methods will now be described herein in detail with reference to FIGS. 17A and 17B.

Figure 17B:
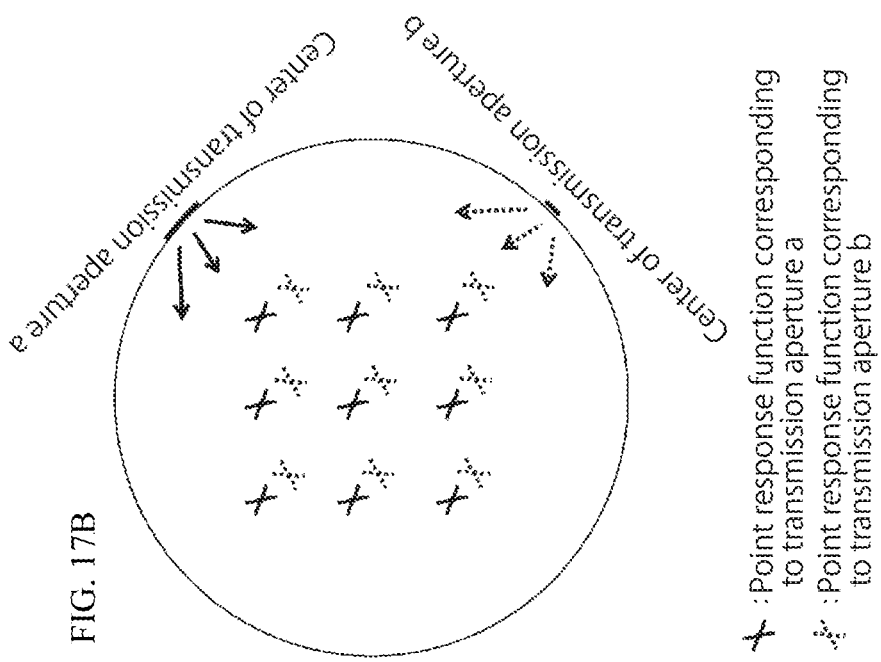
FIGS. 17A and 17B show photos of two methods for processing body motions, the photos illustrating a comparison.
Figure 17A:
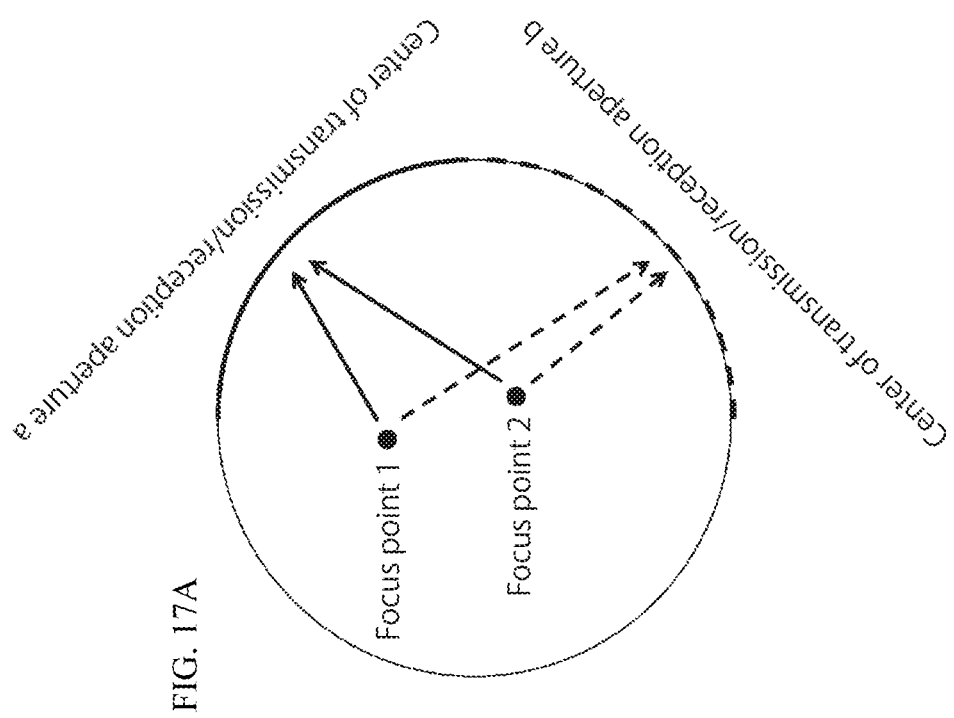

FIG. 17A corresponds to the body motion removal method described in the above 3. A line segment connecting a central point of a transmission/reception aperture (which may be an average value of coordinates xy of elements at both ends of the aperture or a center of gravity, for example) and a focus point is regarded as a vector component to be measured. In either transmission or reception, or both transmission and reception, the aperture is configured so that ultrasonic waves focus on the focal point. Since an image includes a plurality of focus points, a tomographic image is captured by performing focus point scans so that the focus points are distributed across a space.

On the other hand, FIG. 17B corresponds to the body motion removal method described in 4. By narrowing a transmission aperture, no focal point is formed in transmission. In reception, by combining parallel processing corresponding to a plurality of focus points for reception, an image of a plurality of observation points can therefore be captured at a time. By setting transmission apertures at two different positions on the ring, two images of point response functions in different directions can be captured. (In this case, an inclination of a line segment connecting each of the focus points and the central point of the aperture is not constant in a precise sense. As a result, rotation angles of the point response functions also differ from each other in the figure in a precise sense. In here, however, a schematic view in which the inclination and the rotation angles are approximately constant is used for description.) As described above, a body motion is removed by capturing two (or more) images, by compounding the images, by calculating covariance matrices in Casorati matrices, and by performing singular value decomposition.

The following describes the reasons of why it is preferable that an operation of transmission and an operation of reception are asymmetry, such that, in transmission, an aperture is narrowed to blur a focus, while, in reception, the aperture is expanded to focus on each reception focus point. As for transmission of ultrasonic waves, once the ultrasonic waves are transmitted, changing a transmission condition becomes difficult after echo data is acquired. A narrowed aperture therefore is required to deliver energy over an entire imaging area in single transmission. As for reception, as long as echo data is kept maintained with information on reception element numbers, data on a plurality of different focus points for reception can be processed simultaneously. A difference in feature between transmission and reception, as described above, leads to such asymmetric operations.

In the method illustrated in FIG. 17B, capturing an image at higher spatial resolution or contrast resolution by compounding echo signals or by imaging data acquired in a plurality of times under different transmission aperture conditions is also advantageous. In such a case, a sum of sets of elements configuring at least one or a plurality of apertures used to capture a single image is referred to as "region". In acquiring data in the directions A and B, as described above, a sum of sets of apertures is set so that regions do not overlap each other.

Other Embodiments

The embodiment of the present invention has been described above. The present invention is not, however, limited to the embodiment, but variously modified and altered based on the technical idea of the present invention.

In the above described embodiment, the elements transmit pulse Doppler ultrasonic waves, and the elements each function as both a transmission element and a reception element. However, this is merely an example. For example, the elements may transmit continuous wave Doppler ultrasonic waves. In this case, it is advantageous that transmission elements and reception elements be separate elements.

For example, the ultrasonic diagnostic system 10 may perform scanning in an imaging view field by alternately performing a packet used to measure a blood flow amount (in which ultrasonic waves are transmitted and received in a full aperture) and a packet used to measure a flow velocity (in which ultrasonic waves are transmitted and received in a restricted aperture).

Obviously, numerous modifications and variations of the present invention are possible in light of the above teachings. It is therefore to be understood that within the scope of the appended claims, the present invention may be practiced otherwise than as specifically described herein.

What is claimed is:
1. An ultrasonic diagnostic system comprising:
a plurality of elements disposed around a subject, the plurality of elements being configured to transmit and/or receive ultrasonic waves;
a controller configured to control the plurality of elements so that at least some of elements disposed in a first region, among the plurality of elements, transmit ultrasonic waves at a first angle to a diagnosis target in the subject, at least some of elements disposed in a second region, among the plurality of elements, receive reflected waves of the ultrasonic waves, the reflected waves being reflected from the diagnosis target at a second angle, and at least some of elements disposed in a third region, among the plurality of elements, receive reflected waves of the ultrasonic waves, the reflected waves being reflected from the diagnosis target at a third angle distinct from the second angle; and
an operator configured to calculate a velocity vector of the diagnosis target using the reflected waves received by the at least some of the elements disposed in the second region and the reflected waves received by the at least some of the elements disposed in the third region.
2. An ultrasonic diagnostic system comprising:
a plurality of elements disposed around a subject, the plurality of elements being configured to transmit and/or receive ultrasonic waves;
a controller configured to control the plurality of elements so that at least some of elements disposed in a first region, among the plurality of elements, transmit first ultrasonic waves at a first angle toward a diagnosis target in the subject, the at least some of the elements disposed in the first region, among the plurality of elements, receive reflected waves of the first ultrasonic waves, the reflected waves being reflected from the diagnosis target at the first angle, at least some of elements disposed in a second region, among the plurality of elements, transmit second ultrasonic waves at a second angle toward the diagnosis target, and the at least some of the elements disposed in the second region, among the plurality of elements, receive reflected waves of the second ultrasonic waves, the reflected waves being reflected from the diagnosis target at the second angle; and
an operator configured to calculate a velocity vector of the diagnosis target using the reflected waves received by the at least some of the elements disposed in the first region and the reflected waves received by the at least some of the elements disposed in the second region.
3. The ultrasonic diagnostic system according to claim 1, wherein the operator has a mode for measuring a velocity vector and a mode for measuring a flow amount, in measuring a velocity of a fluid flowing into the diagnosis target, and
wherein the plurality of elements includes a first range in which elements that transmit the ultrasonic waves in the mode for measuring a velocity vector are distributed, a second range in which elements that receive the ultrasonic waves transmitted in the mode for measuring a velocity vector are distributed, a third range in which elements that transmit the ultrasonic waves in the mode for measuring a flow amount are distributed, and a fourth region in which elements that receive the ultrasonic waves transmitted in the mode for measuring a flow amount are distributed, the first range being narrower than the third range or the second range being narrower than the fourth range.
4. The ultrasonic diagnostic system according to claim 3, wherein the operator comprises a body motion removal filter configured to set, in the mode for measuring a velocity vector, a cut-off value that is different in each velocity component in the velocity vector.

5. An ultrasonic diagnostic system comprising:
a plurality of elements disposed around a subject, the plurality of elements being configured to transmit and/or receive ultrasonic waves;
a controller configured to control the plurality of elements so that at least some of elements disposed in a first region, among the plurality of elements, receive reflected waves of first ultrasonic waves, the reflected waves being reflected from a diagnosis target in the subject, and at least some of elements disposed in a second region, among the plurality of elements, receive reflected waves of second ultrasonic waves, the reflected waves being reflected from the diagnosis target; and
an operator configured to capture a first image using the reflected waves of the first ultrasonic waves, the reflected waves being received by the at least some of the elements disposed in the first region, to capture a second image using the reflected waves of the second ultrasonic waves, the reflected waves being received by the at least some of the elements disposed in the second region, to calculate two matrices for the respective first and second images in each of which vectors formed by rearranging the image are rearranged in a time direction, to calculate a third matrix in which the two matrices are arranged in a direction perpendicular to the time direction, and to extract information on blood flows in the diagnosis target from the third matrix.

6. An ultrasonic diagnostic system comprising:
a plurality of elements disposed around a subject, the plurality of elements being configured to transmit and/or receive ultrasonic waves;
a controller configured to control the plurality of elements so that at least elements disposed in a first region, among the plurality of elements, transmit first ultrasonic waves toward a diagnosis target in the subject, and at least elements disposed in a second region, among the plurality of elements, transmit second ultrasonic waves toward the diagnosis target; and
an operator configured to capture a first image using reflected waves of the first ultrasonic waves transmitted from the elements disposed in the first region, to capture a second image using reflected waves of the second ultrasonic waves transmitted from the elements disposed in the second region, to calculate two matrices for the respective first and second images in each of which vectors formed by rearranging the image are rearranged in a time direction, to calculate a third matrix in which the two matrices are arranged in a direction perpendicular to the time direction, and to extract information on blood flows in the diagnosis target from the third matrix.

7. The ultrasonic diagnostic system according to claim 5, wherein the operator comprises a filter configured to separate, from the third matrix, a body motion and blood flows to remove the body motion.

8. The ultrasonic diagnostic system according to claim 7, wherein the filter configured to remove the body motion is singular value decomposition or eigen value decomposition.

9. The ultrasonic diagnostic system according to claim 1, wherein the operator sets, when receiving the reflected waves, an independent time axis setting per a reception focus, and uses, in calculating a cross-correlation between signals acquired at different time phases, the independent time axis as an axis for calculating the cross-correlation.

10. An ultrasonic diagnostic method performed by using a diagnostic device that comprises a plurality of elements disposed around a subject, the plurality of elements being configured to transmit and/or receive ultrasonic waves, the ultrasonic diagnostic method comprising:
controlling the plurality of elements so that at least some of elements disposed in a first region, among the plurality of elements, transmit ultrasonic waves at a first angle to a diagnosis target in the subject, at least some of elements disposed in a second region, among the plurality of elements, receive reflected waves of the ultrasonic waves, the reflected waves being reflected from the diagnosis target at a second angle, and at least some of elements disposed in a third region, among the plurality of elements, receive reflected waves of the ultrasonic waves, the reflected waves being reflected from the diagnosis target at a third angle distinct from the second angle; and
calculating a velocity vector of the diagnosis target using the reflected waves received by the at least some of the elements disposed in the second region and the reflected waves received by the at least some of the elements disposed in the third region.

11. An ultrasonic diagnostic method performed by using a diagnostic device that comprises a plurality of elements disposed around a subject, the plurality of elements being configured to transmit and/or receive ultrasonic waves, the ultrasonic diagnostic method comprising:
controlling the plurality of elements so that at least some of elements disposed in a first region, among the plurality of elements, transmit first ultrasonic waves at a first angle toward a diagnosis target in the subject, the at least some of the elements disposed in the first region, among the plurality of elements, receive reflected waves of the first ultrasonic waves, the reflected waves being reflected from the diagnosis target at the first angle, at least some of elements disposed in a second region, among the plurality of elements, transmit second ultrasonic waves at a second angle toward the diagnosis target, and the at least some of the elements disposed in the second region, among the plurality of elements, receive reflected waves of the second ultrasonic waves, the reflected waves being reflected from the diagnosis target at the second angle; and
calculating a velocity vector of the diagnosis target using the reflected waves received by the at least some of the elements disposed in the first region and the reflected waves received by the at least some of the elements disposed in the second region.

12. An ultrasonic diagnostic system comprising:
a plurality of elements disposed around a subject, the plurality of elements being configured to transmit and/or receive ultrasonic waves;
a controller configured to control the plurality of elements so that elements configuring a part of the plurality of elements transmit ultrasonic waves toward a diagnosis target in the subject, and reflected waves of the ultrasonic waves from the diagnosis target are received by two or more apertures disposed in regions where angles of reflection from the diagnosis target differ from each other; and
an operator configured to calculate a velocity vector of the diagnosis target using the reflected waves respectively received by groups of elements configuring the two or more apertures.

13. An ultrasonic diagnostic system comprising:
a plurality of elements disposed around a subject, the plurality of elements being configured to transmit and/or receive ultrasonic waves;
a controller configured to control the plurality of elements so that elements disposed in a first region, among the plurality of elements, transmit first ultrasonic waves toward a diagnosis target in the subject, the elements disposed in the first region receive reflected waves of the first ultrasonic waves, the reflected waves being reflected from the diagnosis target, elements disposed in a second region, among the plurality of elements, transmit second ultrasonic waves toward the diagnosis target, and the elements disposed in the second region receive reflected waves of the second ultrasonic waves, the reflected waves being reflected from the diagnosis target; and
an operator configured to calculate a velocity vector of the diagnosis target using the reflected waves of the first and second ultrasonic waves.

14. The ultrasonic diagnostic system according to claim 2, wherein the operator has a mode for measuring a velocity vector and a mode for measuring a flow amount, in measuring a velocity of a fluid flowing into the diagnosis target, and
wherein, among a first range in which elements that transmit the ultrasonic waves in the mode for measuring a velocity vector are distributed, a second range in which elements that receive the ultrasonic waves transmitted in the mode for measuring a velocity vector are distributed, a third range in which elements that transmit the ultrasonic waves in the mode for measuring a flow amount are distributed, and a fourth region in which elements that receive the ultrasonic waves transmitted in the mode for measuring a flow amount are distributed, the first range is narrower than the third range or the second range is narrower than the fourth range.

15. The ultrasonic diagnostic system according to claim 14, wherein the operator comprises a body motion removal filter configured to set, in the mode for measuring a velocity vector, a cut-off value that is different in each velocity component in the velocity vector.

16. The ultrasonic diagnostic system according to claim 6, wherein the operator comprises a filter configured to separate, from the third matrix, a body motion and blood flows to remove the body motion.

17. The ultrasonic diagnostic system according to claim 16, wherein the filter configured to remove the body motion is singular value decomposition or eigen value decomposition.

18. The ultrasonic diagnostic system according to claim 2, wherein the operator sets, when receiving the reflected waves, an independent time axis setting per a reception focus, and uses, in calculating a cross-correlation between signals acquired at different time phases, the independent time axis as an axis for calculating the cross-correlation.

* * * * *